US009826939B2

United States Patent
Averina et al.

(10) Patent No.: US 9,826,939 B2
(45) Date of Patent: Nov. 28, 2017

(54) SYSTEMS AND METHODS FOR DETECTING MEDICAL TREATMENT

(71) Applicant: Cardiac Pacemakers, Inc., St. Paul, MN (US)

(72) Inventors: Viktoria A. Averina, Roseville, MN (US); Pramodsingh Hirasingh Thakur, Woodbury, MN (US); Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 41 days.

(21) Appl. No.: 14/755,150

(22) Filed: Jun. 30, 2015

(65) Prior Publication Data
US 2016/0000380 A1    Jan. 7, 2016

Related U.S. Application Data

(60) Provisional application No. 62/019,703, filed on Jul. 1, 2014.

(51) Int. Cl.
*A61B 5/00* (2006.01)
*A61B 5/11* (2006.01)
(Continued)

(52) U.S. Cl.
CPC .......... *A61B 5/7275* (2013.01); *A61B 5/0537* (2013.01); *A61B 5/091* (2013.01);
(Continued)

(58) Field of Classification Search
CPC ............ A61B 5/7275; A61B 1/056831; A61B 5/0028
See application file for complete search history.

(56) References Cited

U.S. PATENT DOCUMENTS 7,184,820 B2   2/2007   Jersey-Willuhn et al.
7,577,475 B2   8/2009   Cosentino et al.
(Continued)

FOREIGN PATENT DOCUMENTS

CN   106470598 A        3/2017
WO   WO-2014158800 A1   10/2014
WO   WO-2016004009 A1   1/2016

OTHER PUBLICATIONS

"International Application Serial No. PCT/US2014/20232, International Search Report dated May 12, 2014", 5 pgs.
(Continued)

*Primary Examiner* — Robert N Wieland
(74) *Attorney, Agent, or Firm* — Schwegman Lundberg & Woessner, P.A.

(57) ABSTRACT

Systems and methods are provided for using stored physiologic information about a subject to detect a previous treatment event. Physiologic information can be sensed from a subject using one or more sensors. Using a detection circuit, a change in the sensed physiologic information, such as a change from reference physiologic information, can be used to identify a candidate previous treatment event. An alert or other information about the candidate treatment event can be provided to a patient or clinician. In an example, a candidate treatment event can include a heart failure or diuresis treatment that is identified using information about a change in one or more of a subject's circadian pattern, a subject's thoracic impedance, or a subject's respiration status.

20 Claims, 7 Drawing Sheets

(51) Int. Cl.
*A61B 5/053* (2006.01)
*A61B 7/04* (2006.01)
*A61B 5/091* (2006.01)
*A61N 1/362* (2006.01)
*A61N 1/39* (2006.01)
*A61B 5/0205* (2006.01)
*A61N 1/36* (2006.01)
*A61N 1/365* (2006.01)

(52) U.S. Cl.
CPC .......... *A61B 5/1116* (2013.01); *A61B 5/1118* (2013.01); *A61B 5/4839* (2013.01); *A61B 5/4848* (2013.01); *A61B 5/4857* (2013.01); *A61B 7/04* (2013.01); *A61N 1/3627* (2013.01); *A61B 5/0205* (2013.01); *A61N 1/36114* (2013.01); *A61N 1/36521* (2013.01); *A61N 1/36528* (2013.01); *A61N 1/36535* (2013.01); *A61N 1/36542* (2013.01); *A61N 1/36578* (2013.01); *A61N 1/36585* (2013.01); *A61N 1/39* (2013.01)

(56) References Cited

U.S. PATENT DOCUMENTS

| | | | |
|---|---|---|---|
| 7,647,114 | B2 | 1/2010 | Libbus |
| 7,664,548 | B2 | 2/2010 | Amurthur et al. |
| 7,925,348 | B1 | 4/2011 | Bornzin et al. |
| 8,005,543 | B2 | 8/2011 | Libbus et al. |
| 8,052,610 | B2 | 11/2011 | Bullens et al. |
| 8,052,611 | B2 | 11/2011 | Wariar et al. |
| 8,303,513 | B2 | 11/2012 | Wariar et al. |
| 8,512,252 | B2 | 8/2013 | Ludomirsky et al. |
| 9,339,231 | B2 | 5/2016 | Thakur |
| 2008/0228090 | A1 | 9/2008 | Wariar et al. |
| 2011/0137360 | A1* | 6/2011 | Ternes ............ A61B 5/0028 607/4 |
| 2012/0253207 | A1 | 10/2012 | Sarkar et al. |
| 2012/0259183 | A1 | 10/2012 | Thakur et al. |
| 2012/0296671 | A1 | 11/2012 | Simons-Nikolova et al. |
| 2013/0131506 | A1 | 5/2013 | Pollack |
| 2013/0274705 | A1 | 10/2013 | Burnes et al. |
| 2014/0276164 | A1 | 9/2014 | Thakur et al. |
| 2016/0174904 | A1 | 6/2016 | Thakur et al. |

OTHER PUBLICATIONS

"International Application Serial No. PCT/US2014/20232, Written Opinion mailed May 12, 2014", 10 pgs.
"Understanding Your Ejection Fraction", [Online]. Retrieved from the Internet: <ttp://m y .clev elandclinic.org/heart/disorders/heartfailure/ejectionfraction.aspx>, (Accessed Apr. 18, 2013), 3 pgs.
Blair, John E, et al., "Weight changes after hospitalization for worsening heart failure and subsequent re-hospitalization and mortality in the EVEREST trial", European Heart Journal Jul. 2009 vol. 30, No. 13, (Jul. 2009), 1666-1673.
Damy, Thibaud, et al., "Determinants and prognostic value of pulmonary arterial pressure in patients with chronic heart failure", European Heart Journal 31, (2010), 2280-2290.
Merchant, Faisal M, et al., "Implantable Sensors for Heart Failure", Circulation: Arrhythmia and Electrophysiology 2010; 3, [Online} Retrieved from Internet: <http://circep.ahajournals.org/content/3/6/657.full>, (2010; Accessed Apr. 26, 2013), 657-667.
"U.S. Appl. No. 14/196,494, Notice of Allowance dated Jul. 21, 2015", 5 pgs.
"U.S. Appl. No. 14/196,494, Notice of Allowance dated Dec. 4, 2015", 7 pgs.
"U.S. Appl. No. 15/058,613, Non Final Office Action dated Apr. 7, 2017", 7 pgs.
"U.S. Appl. No. 15/058,613, Preliminary Amendment filed Mar. 3, 2016", 7 pgs.
"International Application Serial No. PCT/US2015/038495, International Preliminary Report on Patentability dated Jul. 12, 2017", 8 pgs.
"International Application Serial No. PCT/US2015/038495, International Search Report dated Sep. 14, 2015".
"International Application Serial No. PCT/US2015/038495, Written Opinion dated Sep. 14, 2015".

* cited by examiner

SYSTEMS AND METHODS FOR DETECTING MEDICAL TREATMENT

CLAIM OF PRIORITY

This application claims the benefit of priority under 35 U.S.C. §119(e) of U.S. Provisional Patent Application Ser. No. 62/019,703, filed on Jul. 1, 2014, which is herein incorporated by reference in its entirety.

BACKGROUND

Congestive heart failure ("heart failure") is a public health concern with a significant economic impact. Subjects with congestive heart failure can require frequent hospitalization or treatment. Hospitalization or treatment for heart failure can include administration of a diuretic drug to a subject to help the subject expel excess fluid, and to thereby relieve some symptoms of congestive heart failure. A decrease in fluid, such as in a subject's thoracic region, can result in an increase in a subject's thoracic impedance or an increase in the subject's average respiratory tidal volume.

Some subjects with congestive heart failure can use wearable or implantable medical devices (IMDs) to treat heart failure and to alleviate symptoms of heart failure. Some examples of IMDs include cardiac function management (CFM) devices such as pacemakers, cardioverter defibrillators (ICDs), cardiac resynchronization devices, neural stimulation devices, cardiac monitoring devices, and devices that include a combination of multiple such capabilities, among other devices. Some devices include one or more sensors to monitor a subject's physiologic status. An IMD can be configured to evaluate a subject's health status using physiologic information received from the sensors. For example, a subject's health status can be evaluated using information from one or more of a thoracic impedance sensor or an accelerometer.

Various techniques can be used to store information in an IMD or to transmit information stored by an IMD to another device. For example, Sarkar et al., in U.S. Patent Application Publication No. US2012/0253207 entitled "Heart Failure Monitoring," refers generally to an IMD that can be configured to transmit higher resolution diagnostic information to a clinician or external device during a hospitalization period, and can be configured to transmit lower resolution diagnostic information during a post-hospitalization period.

OVERVIEW

Systems and methods are described for using stored information about multiple physiologic signals to detect or identify a previous treatment event. A treatment event, such as for heart failure, can occur at various settings, including at a hospital, a subject's home, or a special care facility. In an example, an HF treatment can include admission to a hospital for multiple days. During this multiple day interval, a subject may remain relatively stationary in a hospital bed, or the subject may have otherwise limited mobility. In another example, a subject can receive an intravenous (IV) diuresis treatment. In response to the diuresis treatment, the subject can expel excess thoracic fluid. In another example, a subject can receive one or more inotropic drugs. In response to the drug treatment, the subject can exhibit improved myocardial contractility or cardiac output. Information from physiologic sensors, configured to sense the subject, can include information about a subject's physiologic response to a hospitalization, drug treatment, or other intervention.

The present inventors have recognized, among other things, that a problem to be solved can include accurate identification or reporting of a treatment event, such as a heart failure treatment event. The present subject matter can provide a solution to this problem by identifying one or more candidate treatment events using information about one or more physiologic signals from a subject. In an example, the present subject matter can include using a trend of physiologic signal information, identifying a departure from the trend, and identifying whether the departure from the trend indicates a treatment event.

In an example, the present subject matter includes a system for detecting a previous or ongoing treatment of a subject, including a first physiologic sensor configured to sense a physiologic signal from the subject, and a treatment detection circuit. The treatment detection circuit can include, among other things, a memory circuit configured to store information about the physiologic signal from the first physiologic sensor, and a processor circuit configured to identify a candidate treatment event for the subject using the information about the physiologic signal stored in the memory circuit.

In an example, the present subject matter includes a method for detecting a previous or ongoing treatment of a subject, including receiving, using an ambulatory medical device, physiologic status information about the subject over a first duration from a first physiologic sensor, recording the received physiologic status information about the subject using a memory circuit coupled to the ambulatory medical device, and identifying a candidate treatment event for the subject using a processor circuit and the recorded physiologic status information about the subject from the memory circuit.

In an example, the present subject matter includes an ambulatory medical device that includes a data input configured to receive a physiologic signal from a physiologic sensor, the physiologic sensor configured to sense information about a subject's physiologic status, and a memory circuit configured to store information about the physiologic signal received using the data input. A processor circuit internal to or external from the ambulatory medical device can include a processor circuit that is configured to identify a candidate treatment event using the information about the physiologic signal stored in the memory circuit.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
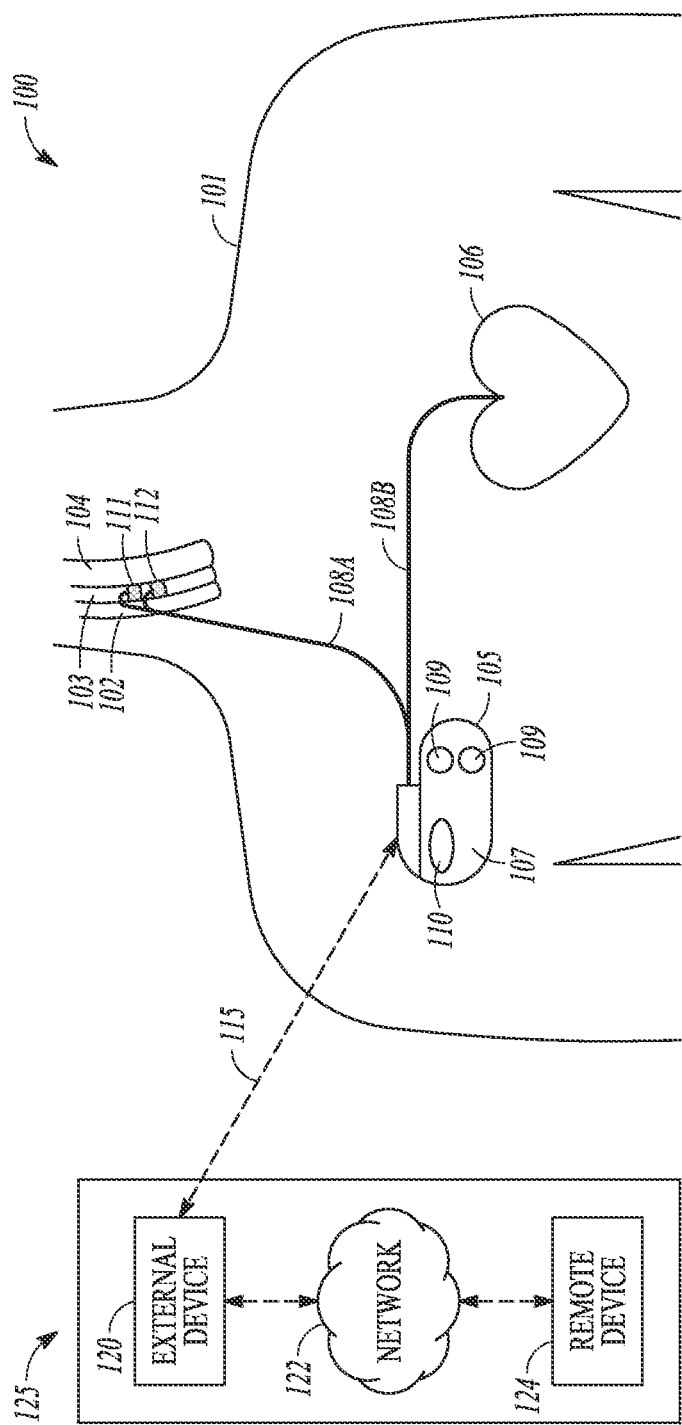
FIG. 1 illustrates generally an example of an implantable medical device in a subject's body.

Congestive heart failure (HF) is a condition that affects pumping efficiency of a heart. Several treatment options are available to patients or subjects who suffer from HF. Generally, subjects who receive an HF treatment or therapy can show some physiologic change in response to the HF treatment or therapy or in response to the circumstances of the treatment or therapy. For example, an HF subject with high blood pressure can receive a blood vessel dilator or angiotensin-converting enzyme (ACE) inhibitor, and in response the subject's blood pressure can be reduced. An HF subject who suffers from fibrillation episodes can be treated with cardiac glycosides, such as digoxin, and in response the chemistry of the subject's cardiac muscle cells can be altered to reduce the likelihood or severity of future episodes. An HF subject who suffers from edema or fluid buildup in the legs or chest can receive a diuretic treatment, for example aldactone, and in response, fluid can be expelled from the subject's system.

Physiologic information about an HF subject can be sensed, for example using an ambulatory or implantable medical device (IMD), and the physiologic information can optionally be stored using a memory circuit that is internal or external to the IMD. Various systems and methods can be used to determine whether a subject previously received a treatment, such as an HF treatment. In an example that includes using a detection circuit, a change in physiologic information sensed from a subject, such as a change from reference physiologic information, can be used to identify a candidate treatment event. A candidate treatment event can include, among other things, a surgical event, an HF hospitalization treatment, a diuresis treatment, an extracellular volume reduction treatment, or a fluid infusion treatment. In an example, an HF hospitalization treatment can include one or more treatments or therapies, such as a diuresis treatment. A hospitalization or treatment event due to some other comorbidity or event can include an IV fluid administration.

A detection circuit or one or more other circuits can be configured to provide an indication of a likelihood that the candidate previous treatment event corresponds to an actual treatment event. The likelihood can include a probability or a confidence that a particular candidate event represents an actual HF hospitalization treatment or an actual diuresis treatment, or some other actual subject intervention. An alert or other information about the subject or about the candidate treatment event can be stored, such as in an IMD, or can be communicated to a patient or clinician, such as via an external interface.

A candidate treatment event can be identified using information about a trend or a change in stored physiologic information about a subject. For example, a trend or change in one or more of a subject's circadian pattern, impedance (e.g., thoracic, cervical, or other impedance, such as measured across one or multiple different impedance vectors), or respiration status, among other physiologic indicators, can be used to indicate a candidate treatment event. That is, the trend or change can indicate that a treatment occurred or may have occurred.

In an example that includes using information about a subject's circadian pattern, a candidate treatment event can be indicated by a relative cessation of a subject circadian pattern. The relative cessation can be derived or inferred using information about a subject's measured physical activity level, impedance, posture, or other information about the subject's physiologic status that can be correlated with the subject's circadian behavior. The relative cessation can correspond to a hospital admission, and can last for several days. An HF subject who is hospitalized can have a relatively low daily physical activity level or a loss of a normal circadian pattern relative to the subject's reference or baseline behavior. The emergence of a subject's circadian pattern, relative to a previous cessation, can correspond to a hospital discharge. A processor circuit can identify a candidate treatment event using information about the subject circadian pattern that was recorded around the time of the hospital admission. For example, low variation in one or more signals corresponding to the subject's physiologic status, such as over a 24-hour period, can indicate a suppression or cessation of the subject's circadian pattern. A subsequent greater variation in one or more signals corresponding to the subject's physiologic status, such as over a 24-hour period, can indicate that a circadian pattern emerged. The processor circuit can identify a candidate treatment event corresponding to the cessation and subsequent emergence of the subject's circadian pattern.

In an example that includes using information about a subject's thoracic impedance, a candidate treatment event can be identified when stored information indicates a change in the subject's thoracic impedance. In response to a diuresis treatment, overall fluid loss can be evidenced by an increase in the subject's thoracic impedance relative to a reference or to a previously-observed impedance (e.g., observed one or more days prior to the treatment). The processor circuit can identify a candidate treatment event corresponding to the relative increase in the subject's thoracic impedance magnitude by a change (e.g., a step-like change) in the signal from a lower to a higher impedance. An opposite response can be expected in response to an IV fluid administration event.

In an example that includes using information about a subject's thoracic impedance, a candidate treatment event that includes a major intervention or major surgical event can be identified when stored impedance information includes a rapid step change, such as a change by greater than a specified threshold impedance amount over a specified duration. Generally, the specified duration can be less than one day, although longer durations can be used. Information about a thoracic impedance signal step change can be used to indicate, among other things, a coronary artery bypass graft (CABG) surgery, an installation of a left ventricular assist device (LVAD), a valve replacement, an intervention that includes some other physical change to a patient's anatomy, or an installation or removal of a device or lead. In an example, information about multiple different thoracic impedance signals, corresponding to multiple different thoracic impedance vectors, can be recorded, averaged over a specified interval, and used to identify a trend or a step change.

For example, a daily impedance signal mean or average corresponding to a first impedance vector can be determined for multiple days, including first, second, third, and fourth days $d_1$-$d_4$. Although impedance signal information for four days is used in this example, fewer or additional days can be similarly used. In this example, the first day corresponds to a present day, the second day corresponds to the day prior to the first day, the third day corresponds to the day prior to the second day, and so on. A mean or average impedance value of the first vector for multiple days can be determined and compared to a mean for multiple other days for the same first vector. For example, a present mean can be determined for $d_1$ and $d_2$, and a delayed mean can be determined for $d_3$ and $d_4$. A difference between the present and delayed means can be determined in aggregate or individually. In an example, a mean of the combination of $d_1$ and $d_2$ is used, and a mean of the combination of the $d_3$ and $d_4$ is used. Optionally, the present mean (corresponding to the combination of $d_1$ and $d_2$) can be expressed as a percentage difference from the delayed mean. If the difference, or percentage difference, exceeds some specified threshold difference amount (e.g., a specified number of ohms or a specified percentage, such as 20%), then a step change can be indicated for the impedance signal corresponding to the first vector. Impedance information from one or more other vectors can be similarly analyzed to determine whether there was a step change corresponding to any other vectors. In an example, when impedance information from multiple different vectors each respectively indicates a step change, then the step change can be identified as being a likely indication of a major intervention or major surgical event. In an example, in response to the indication of a major intervention or major surgical event, one or more baseline or references conditions can be re-set automatically, or can be flagged for consideration by a clinician.

In an example that includes using information about a subject's respiratory tidal volume, a candidate previous treatment event can be identified when the stored physiologic information indicates a change in a subject's respiratory tidal volume. When the subject retains excess pulmonary fluid, such as due to heart failure, the subject's tidal volume can be reduced relative to a reference tidal volume. In response to a diuresis treatment, overall fluid loss can be evidenced by an increase in the subject's tidal volume relative to the reference tidal volume or to a previously-observed tidal volume (e.g., observed one or more days prior to the treatment). The processor circuit can identify a candidate treatment event corresponding to the relative increase in the subject's tidal volume. In some examples, a subject's respiratory tidal volume can correspond to the subject's physical activity level. After admission to a hospital, a subject's tidal volume can be decreased relative to the subject's reference tidal volume because the subject may be confined to a hospital bed, and the subject's respiration requirements are reduced. The processor circuit can identify a candidate treatment event corresponding to the change in tidal volume.

A processor circuit or detection circuit can thus use any one or more of information about a subject's circadian pattern, impedance, or respiratory tidal volume, or can use information about some other indication of a subject's physiologic status, to identify that a subject received, or may have received, a treatment. The processor circuit can additionally or alternatively use the information about the subject's physiologic status to detect other events, including a thoracic surgery or pocket revision (e.g., corresponding to a sudden and/or significant change in thoracic impedance), or to detect a physiological effect of device reprogramming (e.g., corresponding to a sudden shift in S1 timing or amplitude, a change in a systolic timing interval, or a heart rate change, such as due to a lower rate limit adjustment). Information about the identified candidate treatment event can optionally be provided to a clinician or to a patient management system, such as in response to a device interrogation or data request initiated by a clinician or by the patient management system. The information provided about the candidate treatment event can optionally include the subject's stored physiologic signal information corresponding to the timing of the identified candidate treatment event.

Information about the candidate treatment event can be used to trigger a specified type of an alert algorithm, such as automatically using an IMD or using an external system that can be communicatively coupled to an IMD. For example, the information can be used to trigger or generate an alert that the subject's HF condition is worsening, and that the subject should be readmitted to a hospital for treatment. In another example, the information about the candidate treatment event can be used to trigger or generate an alert that the subject's HF condition is improving and an HF therapy, such as automatically provided by an IMD, should be adjusted accordingly.

In an example, information about the candidate treatment event can be used to alert a clinician to review medical records or other subject-specific history. For example, information about the candidate treatment can be brought to the attention of a clinician or caregiver, such as via a patient management system, so that the clinician or caregiver can attempt to identify a root cause of a subject's health status change, or to indicate a need for further review of a subject's health status, such as using physiologic information about the subject from other sensors or sources. In an example, an effectiveness of the candidate treatment event can be determined by the processor circuit, such as by identifying a characteristic of the subject's physiologic signal information that indicates a return to a reference health status. Information about the determined effectiveness can be provided to the clinician or caregiver.

Information about the candidate treatment event can be used to disable an alert algorithm or to switch to a different alert algorithm, such as to prevent false-positives. For example, if a subject was recently admitted to a hospital or is undergoing a treatment (e.g., an IV fluid administration treatment, an extracellular volume reduction treatment, etc.), an alert for a candidate treatment event can be suppressed for a specified duration (e.g., a number of hours or days) until after the treatment event is completed. Once the treatment event is indicated or determined to be completed, the alert algorithm can resume. In an example, a sudden shift in a physiologic signal (e.g., an S1 amplitude change after AVD reprogramming) can indicate an automatic recalculation of an alert algorithm reference, or can disable an alert algorithm until a new reference is determined or received.

Referring now to FIG. 1, an implantable or external system can include one or more sensors that can be used to monitor one or more respective physiologic signals from a subject. FIG. 1 illustrates generally an example 100 of a subject 101 with an implantable system. The implantable system can optionally be used to provide a subject therapy or to detect or receive subject physiologic information, such as including impedance information, heart sound information, physical activity level information, respiration information, physiologic pulsatile signal information, or other information about the subject. In an example, the system can be configured to use physiologic information from the subject 101, such as received from one or more physiologic sensors, to identify a subject's health status after a treatment, such as a hospitalization treatment or diuretic treatment.

In FIG. 1, the implantable system includes an implantable medical device (IMD) 105. The implantable medical device 105 can be configured to be coupled to one or more of a first implantable lead system 108A and a second implantable lead system 108B. The first implantable lead system 108A is configured to interact with nerve tissue or cervical vessels in the body of the subject 101, and the second implantable lead system 108B is configured to interact with cardiac tissue.

Examples of the IMD 105 include, without limitation, a pacemaker, a defibrillator, a cardiac resynchronization therapy (CRT) device, an implantable diagnostic device, an implantable loop recorder, or a combination of multiple such devices. The IMD 105 can include transvenous, non-implantable, or subcutaneous systems (with or without venous access or a therapy delivery function). The IMD 105 should be understood to be an example only, and it is contemplated that other electronic medical systems can be used or configured to perform the medical treatment detection functions described herein. For example, a wearable medical device (e.g., a diagnostic device, loop recorder, or a device to provide therapy) can additionally or alternatively be used. A wearable medical device can include one or more surface electrodes (e.g., electrodes for skin contact) to sense a cardiac signal such as an electrocardiograph (ECG) or to sense one or more other physiologic signals from a subject. A wearable medical device can include one or more other sensors, such as a physical activity level sensor, an acoustic sensor, a blood pressure sensor, an oximetry sensor, a respiration sensor, or other sensor configured to receive or monitor information about a subject's physiologic status.

The first implantable lead system 108A coupled to the IMD 105 can include at least one neural stimulation lead that can be subcutaneously implanted to position electrode(s) to stimulate a neural target in a cervical region (e.g., in a region at or near the neck) in the subject 101. Examples of cervical neural targets include a vagus nerve, a carotid sinus nerve, a hypoglossal nerve, a glossopharyngeal nerve, a phrenic nerve, baroreceptors and the nerves that innervate and are proximate to the baroreceptors, and chemoreceptors and the nerves that innervate and are proximate to the chemoreceptors. The neural target may be on the left side (e.g. left vagus nerve), or the right side (e.g. right vagus nerve). Other neural stimulation lead(s) can include electrodes configured to stimulate neural targets outside of a cervical region.

Implanted electrode(s) disposed proximal to or in contact with a neural target can be used to provide neural electrostimulation. A first electrode 111, such as a first nerve cuff electrode, can be disposed at the end of the neural stimulation lead. In an example, the first electrode 111 can include a nerve cuff electrode that can be sized, shaped, or otherwise configured to be disposed around a vagus nerve 103. One or more additional nerve cuff electrodes, such as a second electrode 112, can be similarly provided. In an example, neural stimulation may be provided using the first and second electrodes 111 and 112 in a bipolar configuration. In an example, neural, neural or muscular electrical activity can be detected using the first and second electrodes 111 and 112, or an electrical response signal can be provided and/or detected using the first and second electrodes 111 and 112. One or more other electrodes can be sized, shaped, or otherwise configured to be fed into a vessel near the vagus nerve 103, such as for using electrodes positioned within the vessel to intravascularly stimulate the neural target. For example, a neural target can be stimulated using at least one electrode positioned internally within a jugular vein 102 or a carotid artery 104. The neural stimulation can include bipolar stimulation or unipolar stimulation, such as where a conductive housing 107 of the IMD 105 functions as an electrode.

The IMD 105 can be coupled to a second implantable lead system 108B. The second implantable lead system 108B can include a cardiac electrostimulation stimulation lead that can be subcutaneously implanted to position one or more electrodes to stimulate cardiac tissue of a heart 106, such as myocardial or neural cardiac tissue. In an example, the second implantable lead system 108B can include one or more atrial or ventricular leads, and each lead can include one or more electrodes for pacing and/or cardioversion/defibrillation.

The IMD 105 can include a processor circuit 110 operably connected to one or more of a stimulation circuit or a sensing circuit. The IMD 105 can be configured to operate autonomously with all circuitry residing within the IMD 105, and/or may be configured to operate with one or more other devices (e.g., other IMD(s) and/or external device(s) such as a programmer or an analyzer circuit). The IMD 105 can be configured to deliver neural stimulation therapy and to communicate with a different cardiac rhythm management (CRM) device, such as a pacemaker or defibrillator, which can be configured to sense a physiologic parameter or physiologic response and provide cardiac rhythm management therapy.

One or more leadless ECG electrodes 109 or other electrodes can be disposed on the housing of the IMD 105. These electrodes can be used to detect a heart rate, a cardiac arrhythmia, or other characteristic of a subject's cardiac activity. For example, information received from the leadless ECG electrodes 109 can be received and analyzed by the processor circuit 110 to identify features of a subject electrogram, such as to identify fiducials or points of interest on a QRS complex.

A heart failure analysis module can include one or more of the IMD 105 and an external system 125. The heart failure analysis module can include one or more processor circuits, such as the processor circuit 110 in the IMD 105 or one or more other processor circuits in the external system 125 that can receive information from a physiologic sensor and provide an indication of a subject's health status, such as a subject's heart failure status. In an example, the IMD 105 can include a communication circuit and antenna, or telemetry coil, such as can be used to communicate wirelessly with the external system 125 or other device.

The external system 125 can include an IMD programmer or one or more other remote external circuits (e.g., outside of wireless communication range of the IMD 105 antenna, but coupled to the IMD 105 using an intermediate device, such as a repeater or network access point). The external system 125 can include one or more processor circuits configured to process information that can be sent to or received from the IMD 105. The information can include medical device programming information, subject-specific physiologic sensor data, other device data, instructions, alerts, or other information. In an example, the external system 125 includes an external device 120 configured to display information (e.g., information received from the IMD 105) to a user. The external system 125 can include a programmer configured to communicate information from the IMD 105 to a user or physician, such as by sending an alert (e.g., via e-mail) about a status of the subject 101 or the system 100.

A telemetry link 115 can provide bidirectional communication between the IMD 105 and the external system 125. In an example, the external system 125 includes a programmer. In another example, as illustrated in FIG. 1, the external system 125 can include a patient management system including an external device 120 in close physical proximity of the IMD 105, a remote device 124 in a location relatively distant from the IMD 105, and a communication network 122 that links the external device 120 and the remote device 124. In an example, the external system 125 is a patient management system that permits access to the IMD 105 from a remote location, such as for monitoring a subject's status or adjusting a subject's therapy or a device parameter.

Figure 2:
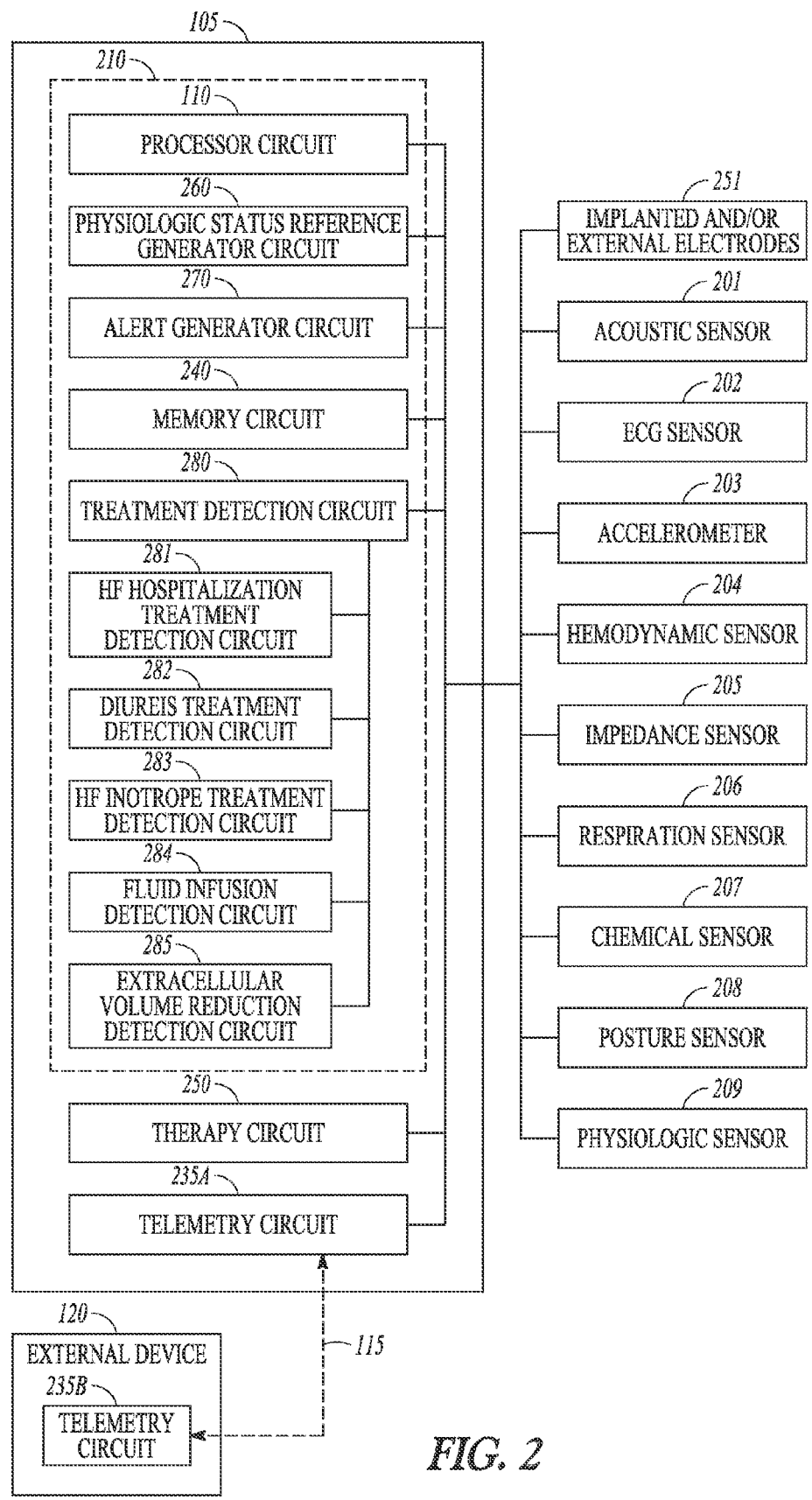
FIG. 2 illustrates generally a diagram of an implantable medical device that includes or is coupled to multiple physiologic sensors.

FIG. 2 illustrates generally an example of the IMD 105. The IMD 105 includes a detection circuit 210. In an example, the detection circuit 210 is a previous treatment detection circuit configured to identify a candidate treatment event for a subject. That is, the detection circuit 210 can be configured to detect one or more previous treatment events, or candidate treatment events. The detection circuit 210 can optionally include one or more of the processor circuit 110 and a memory circuit 240. In the example of FIG. 2, the IMD 105 includes a therapy circuit 250 that can include an electrical energy generator or delivery circuit. The therapy circuit 250 can be configured to use a current or voltage source to deliver an electrical signal between two or more electrodes (e.g., using one or more electrodes included in the first or second implantable lead systems 108A and 108B). In an example, the therapy circuit 250 is coupled to a neural or cardiac electrostimulation circuit comprising implanted and/or external electrodes 251 that are configured to provide electrostimulation to one or more targets.

In the example of FIG. 2, a telemetry circuit 235A in the IMD 105 is connected to the processor circuit 110. The telemetry circuit 235A can transmit data from the IMD 105 to an adjunct system, such as the external device 120. The external device 120 can include a second telemetry circuit 235B that is configured to receive information from the telemetry circuit 235A in the IMD 105. Data transmitted using the telemetry link 115 can include, among other things, data from one or more sensors coupled to the IMD 105, diagnostic information generated by the IMD 105 or the external device 120, or device configuration or programming information for or about the IMD 105.

The detection circuit 210 is coupled to physiologic sensors using respective sensor data inputs. For example, a first sensor data input of the detection circuit 210 can include an input to the processor circuit 110, and the first sensor data input can be coupled to one or more of an acoustic sensor 201, a device-based or other ECG sensor 202, an accelerometer 203, a hemodynamic sensor 204, an impedance sensor 205, a respiration sensor 206, a chemical sensor 207, a posture sensor 208, or other physiologic sensor 209. Information received using a sensor data input of the detection circuit 210 can be stored locally in the IMD 105 using the memory circuit 240, or can be stored externally to the IMD 105 using a different memory circuit included in the external system 125 (see FIG. 1).

The processor circuit 110 can be configured to calculate or determine subject diagnostic information (e.g., ejection fraction, pre-ejection period, etc.) using information received from one or more of the physiologic sensors. In an example, the detection circuit 210 includes a data output that is configured to provide an indication of a candidate treatment event using information from the memory circuit 240 or using physiologic information about the subject from another memory circuit in the external system 125.

Physiologic signal information from multiple different sensors can be acquired and stored, such as before, during, or after a treatment event. A treatment event can include, among other things, a device implant or other procedure, a hospitalization event, a clinical treatment, or a drug administration event. Physiologic information about a subject received from some sensors (e.g., sensors of a first type, such as weight sensors, oximetry sensors, heart rate sensors, ECG sensors, vessel pressure sensors, etc.) can change more than physiologic information about the subject from other sensors (e.g., sensors of a different second type), such as in response to the same treatment or duration. In an example, a more variable characteristic of a physiologic signal can represent an aspect of a subject clinical status or physiology that is more affected by, or responsive to, the treatment, and can thus be representative of the treatment effect. For example, a subject admitted to a hospital for heart failure can be treated with diuretics. If the treatment is effective, the subject may lose weight during or after the treatment. Accordingly, the subject's weight change can be an indication of the treatment effect on the subject. In an example, the subset of sensors that receive or provide the characteristic information that changes most can be monitored, such as following subject discharge, as described in Thakur et al., U.S. patent application Ser. No. 14/196,494, titled "Heart Failure Management to Avoid Rehospitalization", which is hereby incorporated herein by reference in its entirety. As explained in Thakur, a change in information received by a subset of sensors, such as toward values that correspond to a subject hospitalization period, can indicate worsening subject health status, or can indicate that a subject treatment regimen is losing its efficacy. Such an indication can be used to generate an alert to a clinician or subject, or can be used to automatically change an IMD subject monitoring status, an IMD therapy, or other therapy. In an example, the detection circuit 210 can be configured to analyze information from the subset of sensors to identify a prior candidate treatment event.

The acoustic sensor 201 can be coupled to the detection circuit 210. The acoustic sensor 201 can be an implantable or external transducer, such as a microphone or accelerometer. The acoustic sensor 201 can be configured to receive acoustic vibrational energy from a subject, such as including energy in the audible spectrum. In an example, the detection circuit 210 can be configured to receive a data signal that includes information from the acoustic sensor 201, and can be configured to identify one or more of heart sound information, respiration information, or other physiologic information about the subject. For example, information from the acoustic sensor 201 can be used to identify an S1 heart sound timing or amplitude characteristic, or to identify a presence or amplitude characteristic of an S3 or S4 heart sound.

The ECG sensor 202 can be coupled to the detection circuit 210. The ECG sensor 202 can be an implantable or external sensor. For example, the ECG sensor 202 can include at least two electrodes disposed in or on the subject 101 and can be configured to detect electrical activity from the subject 101. In an example, the ECG sensor 202 includes two electrodes (e.g., a can electrode and a remote electrode disposed in or on the heart 106, such as included in the second implantable lead system 108B) implanted in the subject 101. The detection circuit 210 can be configured to receive a data signal that includes electrogram information from the ECG sensor 202. In an example, the detection circuit 210 can use the received electrogram information to identify a morphological characteristic (e.g., a timing, amplitude, shape, etc.) of a subject's QRS complex for one or more cardiac cycles.

The accelerometer 203 or vibration sensor can be coupled to the detection circuit 210. The accelerometer 203 can be an implantable or external sensor. The accelerometer 203 can be configured to receive acceleration or orientation information from a subject, and that information can be used to identify one or more of cardiac activity, respiratory activity, or other physical activity level of a subject, such as a relative exercise or exertion level. The detection circuit 210 can be configured to receive a data signal from the accelerometer 203 and to use the data signal from the accelerometer 203 to identify one or more of heart sound information, respiration information, or other physiologic information about the subject.

The hemodynamic sensor 204 can be coupled to the detection circuit 210. The hemodynamic sensor 204 can be an implantable or external pressure sensor, such as an implantable sensor configured to continuously or intermittently monitor intracardiac or vessel pressure. In an example, the hemodynamic sensor 204 can include a pressure sensor coupled to a right ventricular lead or atrial lead of the IMD 105, or the hemodynamic sensor 204 can alternatively or additionally include a pressure sensor disposed in a pulmonary artery. The detection circuit 210 can be configured to receive a data signal that includes pressure information from the hemodynamic sensor 204.

The impedance sensor 205 can be coupled to the detection circuit 210. The impedance sensor 205 can be implantable or can be external to the subject 101, or can include both implantable and external portions. In an example, the impedance sensor 205 includes at least two electrodes disposed in or on the subject 101 and is configured to detect electrical signals from the subject 101, such as in response to a non-tissue-stimulating electrostimulation provided to the subject 101 using the same or different at least two electrodes. In an example, the impedance sensor 205 includes two implanted electrodes including a can electrode and a remote electrode disposed in, on, or near the heart 106, such as included in the second implantable lead system 108B. The detection circuit 210 can be configured to receive a data signal that includes electrical signal information from the impedance sensor 205, and the processor circuit 110 can use the received data signal to determine an impedance, such as an average, RMS, or other measure of impedance, between the two or more electrodes. In an example, the detection circuit 210 can use the received impedance information to identify a thoracic fluid status, cardiac activity, respiratory activity, muscle activity, a vessel dimensional change, such as using plethysmography techniques, or other information about a subject physiologic status.

The respiration sensor 206 can be coupled to the detection circuit 210. The respiration sensor 206 can be an implantable or external respiration sensor, such as an implantable sensor configured to monitor subject chest expansion and contraction. In an example, the respiration sensor 206 can be configured to provide a data signal that includes information about a subject tidal volume, minute ventilation, respiration rate, or other respiration status. The detection circuit 210 can be configured to receive the data signal from the respiration sensor 206.

The chemical sensor 207 can be coupled to the detection circuit 210. The chemical sensor 207 can be an implantable or external sensor configured to identify one or more biomarkers. For example, the chemical sensor 207 can be configured to detect subject chemistry information, such as including information about one or more of a subject blood chemistry (e.g., electrolytes, glucose, pH, oxygen level, carbon dioxide level, etc.), natriuretic peptides (i.e., B-type natriuretic peptide (BNP), N-terminal proBNP, atrial natriuretic peptide, etc.), inflammatory markers, oxidative stress markers, or collagen turnover or extracellular matrix peptides, among other information. The detection circuit 210 can be configured to receive a data signal that includes chemical status information from the chemical sensor 207.

The posture sensor 208 can be coupled to the detection circuit 210. The posture sensor 208 can be an implantable or external posture sensor configured to detect, determine, or differentiate between one or more subject postures or orientations. The posture sensor 208 can include an accelerometer (such as the accelerometer 203) that is configured to provide information about whether the sensor (e.g., installed in or otherwise coupled to the subject) is oriented vertically or horizontally. In an example, the posture sensor 208 includes an impedance sensor that is configured to measure a thoracic or vessel impedance from which subject orientation can be determined. The detection circuit 210 can be configured to receive a data signal from the posture sensor 208.

In an example, at least one other physiologic sensor 209 can be coupled to the detection circuit 210, and the at least one other physiologic sensor 209 can sense information about one or more other aspects of a physiologic or health status of a subject. The detection circuit 210 can be configured to receive a data signal from the at least one other physiologic sensor 209. In an example, the at least one other physiologic sensor 209 includes a physiologic response to activity (PRA) sensor that provides information about a subject's physiologic status at fixed levels or ranges of physical activity.

The memory circuit 240 can be coupled to the processor circuit 110 and/or to one or more of the physiologic sensors 201-209, such as to receive and store physiologic signal information about a subject's physiologic status over time. In an example, the processor circuit 110 can access the physiologic status information stored in the memory circuit 240 and can be configured to identify a change or a trend in one or more of the physiologic signals. For example, heart sound timing or amplitude information received using the acoustic sensor 201 can be stored in the memory circuit 240, and a trend of the heart sound information can be analyzed using the processor circuit 110 to identify an increasing or decreasing heart sound timing interval or amplitude over time.

The processor circuit 110 can modify or otherwise process information stored in the memory circuit 240, such as to transform one or more physiologic signals. For example, the processor circuit 110 can be configured to generate one or more of a derivative waveform, a filtered waveform, or an integrated waveform of an impedance signal provided by the impedance sensor 205. Such transformation can be implemented with, for example, a differentiator, a filter (e.g., linear, high pass, low pass, band pass), a derivative circuit, or an integrator circuit, among others, such as can be integrated with or coupled to the processor circuit 110. In an example, the modified or processed physiologic signal information can be stored using the memory circuit 240 or analyzed using the processor circuit 110 to identify a candidate treatment event.

The processor circuit 110 can include or can be coupled to a physiologic status reference generator circuit 260. The physiologic status reference generator circuit 260 can be configured to receive information from one or more of the physiologic sensors 201-209 and to generate a subject reference using the received information. In an example, as a subject approaches heart failure, experiences an acute heart failure event, or otherwise experiences an adverse health event, physiologic information about the subject from multiple sensors of different sensor types is likely to change or deviate from respective reference or baseline values. A reference or baseline value can include short-term or long-term data that can be previously specified, can be subject-specific, or can be based on data from a specified population.

For example, a subject thoracic impedance sensor can be configured to measure average thoracic impedance for a subject, such as during a specified time interval during each of multiple days. If the subject is in good or stable health, the average thoracic impedance information can be used to establish a subject-specific thoracic impedance reference value. As the subject approaches heart failure, information about the subject's thoracic impedance can be expected to depart from the previous, subject-specific thoracic impedance reference value.

The physiologic status reference generator circuit 260 can be configured to generate the subject reference using information that is pre-set or specified by a clinician. The pre-set or specified information can be used alone or in combination with subject-specific information (e.g., received using the impedance sensor 205) to generate the subject reference.

Information about a candidate treatment event can be used to update a subject reference, such as for an alert algorithm. In an example, a subject reference physiologic signal value can be continuously updated using information sensed from the subject. When the processor circuit 110 identifies a candidate treatment event, the subject's physiologic information corresponding to the candidate treatment event can optionally be removed from the reference. In this manner, data that may be contaminated by an adverse health event or declining health status can be removed or its influence on the subject reference can be reduced.

The processor circuit 110 can include or can be coupled to a previous treatment detection circuit 280. The treatment detection circuit 280 can be configured to recognize or identify a candidate treatment event using physiologic signal information about the subject, such as can be received from the memory circuit 240. In an example, the treatment detection circuit 280 includes an HF hospitalization treatment detection circuit 281. The HF hospitalization treatment detection circuit 281 is configured to use information from the memory circuit 240 to provide an indication that the subject was or may have been hospitalized for treatment of the subject's heart failure.

In an example, the treatment detection circuit 280 includes a diuresis treatment detection circuit 282. The diuresis treatment detection circuit 282 is configured to use information from the memory circuit 240 to provide an indication that the subject received or may have received a diuretic, such as in response to a detected subject fluid loss. In an example, the treatment detection circuit 280 includes an HF inotrope treatment detection circuit 283. The HF inotrope treatment detection circuit 283 is configured to use information from the memory circuit 240 to provide an indication that the subject received or may have received an inotropic drug for treatment of the subject's heart failure. In an example, the treatment detection circuit 280 includes a fluid infusion detection circuit 284. The fluid infusion detection circuit 284 is configured to use information from the memory circuit 240 to provide an indication that the subject received or may have received a fluid infusion, such as an IV fluid infusion.

In an example, the treatment detection circuit 280 includes an extracellular volume reduction detection circuit 285. The extracellular volume reduction detection circuit 285 is configured to use information from the memory circuit 240 to provide an indication that the subject received or may have received an extracellular volume reduction, such as for treatment of the subject's heart failure. The treatment detection circuit 280 can include one or more other types of detection circuits, for example, an ultrafiltration treatment detection circuit. In an example, an ultrafiltration treatment detection circuit can be configured to identify a subject who has had excess salt or water removed from the subject's body, such as to alleviate a fluid overload condition. An ultrafiltration treatment can be performed in coordination with a diuretic treatment.

The processor circuit 110 can include or can be coupled to an alert generator circuit 270. The alert generator circuit 270 can be configured to use a subject reference, such as generated using the physiologic status reference generator circuit 260, to provide a treatment alert to a subject or to a clinician, to archive an alert using the memory circuit 240, or to communicate an alert to the external system 125. In an example, the alert generator circuit 270 can use information from the treatment detection circuit 280 together with information about a subject reference from the physiologic status reference generator circuit 260 to generate an alert for the subject or for a clinician.

The alert generator circuit 270 can use stored or real-time information from one or more of the physiologic sensors 201-209 to generate the treatment alert. The treatment alert can include, among other things, an indication that a subject experienced a treatment event (e.g., received a treatment, therapy, or other intervention) at a specified time. The treatment alert can optionally include information about the physiologic signal or signals used by the processor circuit 110 to determine that the subject received the treatment, or can include information about one or more other physiologic signals from the subject that correspond in time with the identified treatment event. In an example, the treatment alert provided to a clinician includes a list of available physiologic signal information that the clinician can optionally access from the memory circuit 240 or from another memory circuit in the external system 125.

Figure 3:
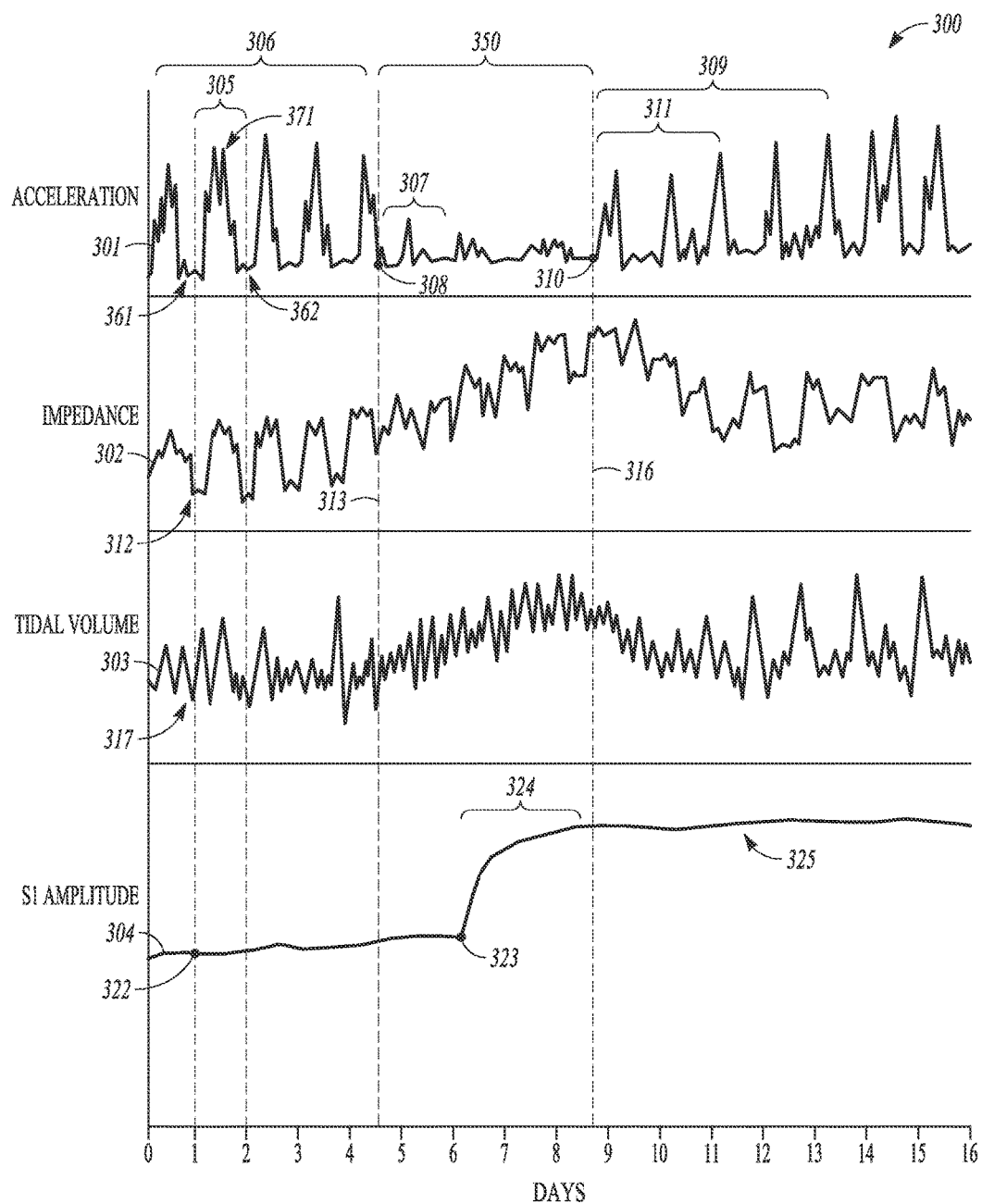
FIG. 3 illustrates generally a first example that includes multiple physiologic signals from a subject and a first treatment event.
Figure 4:
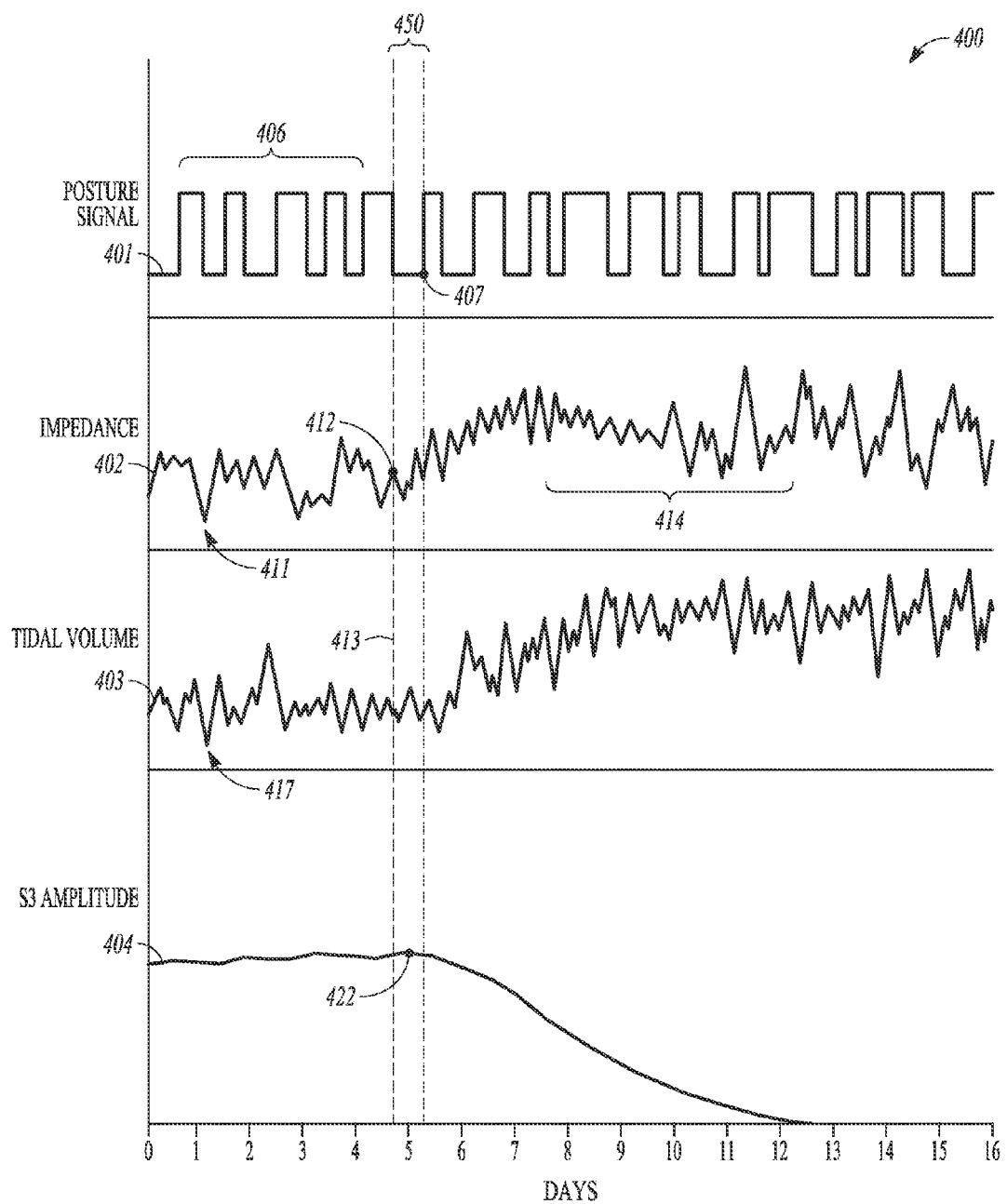
FIG. 4 illustrates generally a second example that includes multiple physiologic signals from a subject and a second treatment event.
Figure 5:
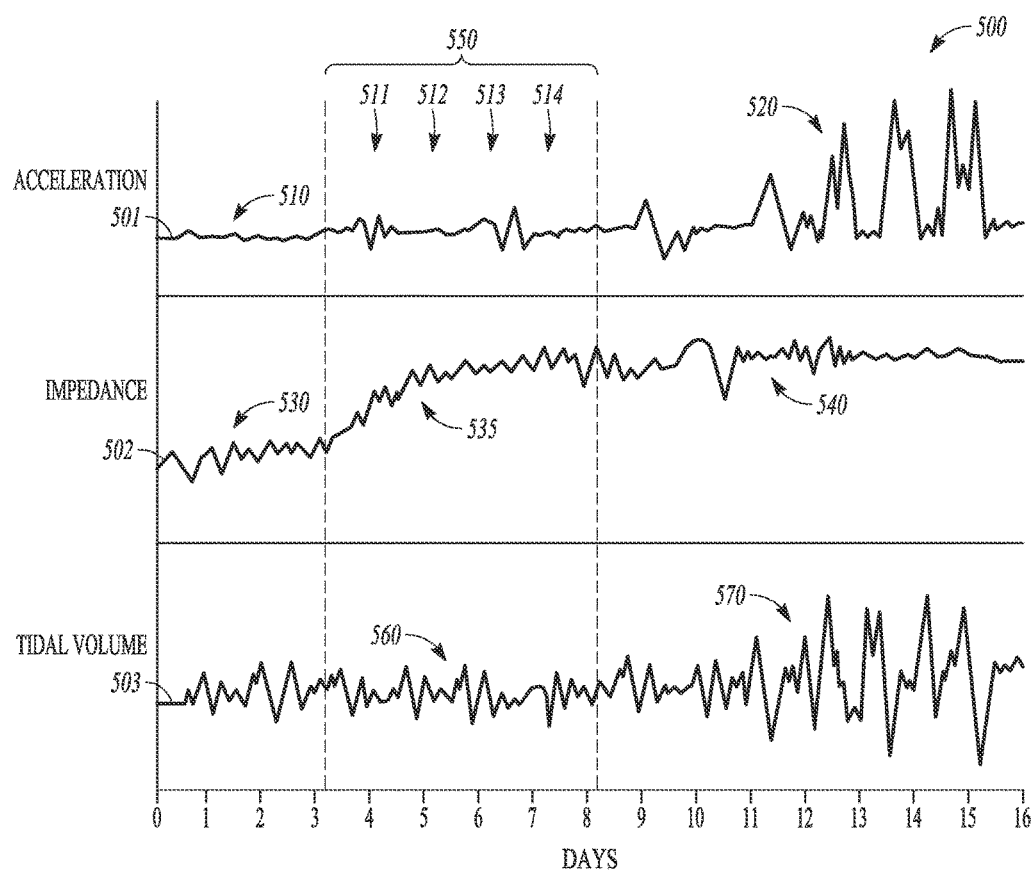
FIG. 5 illustrates generally a third example that includes multiple physiologic signals from a subject and multiple treatment events.

FIGS. 3-5 illustrate generally examples that show one or more changes in previously-acquired physiologic signal information from a subject, and the one or more changes correspond to a treatment event or a candidate treatment event. FIGS. 6-9 illustrate generally examples that show how a candidate treatment event can be identified using information about the previously-acquired physiologic signal information. The one or more changes in a subject's physiologic signal information can be identified using signal information that is stored in the memory circuit 240. The one or more changes can correspond generally to a treatment event, such as a hospitalization, a diuretic administration, an inotrope administration, a fluid infusion, a extracellular volume reduction, or other event.

A treatment event, as referred to herein, can include a hospitalization, an outpatient treatment, an in-home or in-clinic treatment, therapy, or other intervention to effect change in a subject's physiologic status. A hospitalization can include, among other things, a period during which a subject resides in a hospital or other facility for rest, observation, test administration, or to receive a therapy. A candidate treatment event can correspond to a previous interval or point in time that can be identified using the treatment detection circuit 280, and that may correspond to an actual treatment event.

Referring now to FIG. 3, an example 300 includes information about multiple physiologic signals sensed from a subject over multiple days. The example 300 includes information about the multiple physiologic signals before, during, and after a first treatment event 350, such as a hospitalization event or other therapy administration event. In the example of FIG. 3, the first treatment event 350 is an interval that includes about four contiguous days. The example of FIG. 3 includes a pre-treatment interval 306, the first treatment event 350, and a post-treatment interval 309.

The processor circuit 110 can be configured to identify a candidate treatment event using information about one or more of an acceleration signal 301, a thoracic impedance signal 302, a respiratory tidal volume signal 303, or a heart sound signal, such as an S1 heart sound amplitude signal 304. One or more other physiologic signals can additionally or alternatively provide physiologic information that can be used to identify a candidate treatment event for a subject. The acceleration signal 301 can be received using the accelerometer 203. The thoracic impedance signal 302 can be received using the impedance sensor 205. The respiratory tidal volume signal 303 can be received using the respiration sensor 206. The heart sound signal 304 can be received using the accelerometer 203, the acoustic sensor 201, or another sensor or transducer configured to sense heart sound amplitude information (e.g., S1, S2, S3, or S4 amplitude information).

The acceleration signal 301 can represent a smoothed or an average acceleration signal. For example, the acceleration signal can be intermittently sampled, and the resulting samples can be averaged to provide information about a posture, a vibration magnitude, or other movement of a subject over time, or a characteristic physical activity level within a specified physical activity level range. In the example of FIG. 3, the acceleration signal 301 includes physical activity level information over about sixteen days. The physical activity level information is sampled about one time every thirty minutes, and the results can optionally be smoothed and plotted as shown. Other sampling intervals can alternatively be used.

Information about a subject's circadian pattern can be identified or inferred using the physical activity level information from the acceleration signal 301. In the example of FIG. 3, a first interval 305 can correspond to a single day or a 24 hour interval, such as beginning at midnight on a first day and ending at midnight on a second day. The first interval 305 includes a first minimum interval 361 that corresponds to a minimum physical activity level of the subject, such as during a subject's nighttime sleep interval. The first interval 305 includes a first maximum interval 371 that corresponds to an elevated physical activity level of the subject, such as corresponding to a subject's waking hours or an active interval. The first interval 305 includes a second minimum interval 362 that corresponds to a subsequent minimum physical activity level of the subject, such as corresponding to an interval of reduced activity, such as a subsequent resting or nighttime sleep interval. The intervals of relative maximum and minimum physical activity levels can be generally periodic with a 24 hour cycle, and can thus indicate a subject's circadian pattern or sleep/wake cycle.

A change in a subject's circadian pattern can be identified, such as using the processor circuit 110. In the example of FIG. 3, the subject's usual circadian pattern is interrupted during day 4 at the onset 313 of the first treatment event 350. In this example, the first treatment event 350 can include a hospitalization during which the subject is generally confined to a hospital bed for rest or observation. In a second interval 307 during a portion of the first treatment event 350, the peak magnitude of the subject's acceleration signal 301 indicates that the subject's physical activity level is reduced, such as relative to the pre-treatment interval 306. In an example where the subject is known to suffer from heart failure, the relative reduction in the average amplitude of the subject's acceleration signal 301 during the second interval 307 can indicate an abnormal circadian pattern, which can in turn indicate that the subject may have been hospitalized.

At 310, corresponding to an end of the first treatment event 350, the acceleration signal 301 indicates that the subject's circadian pattern resumed. In an example, the acceleration signal 301 can indicate a trend toward a normal or pre-treatment physical activity level over one or more days 311 as the subject resumes normal daily activities, and a regular circadian pattern emerges.

The thoracic impedance signal 302 can be received using the impedance sensor 205 or using the implanted and/or external electrodes 251. The impedance signal 302 can represent a smoothed or an average impedance magnitude signal received from one or more sources and can represent a subject's relative thoracic impedance over time. For example, the impedance signal 302 can represent an intermittently sampled, single impedance vector, and the resulting samples can be averaged to provide a daily average subject thoracic impedance level.

In the example of FIG. 3, the impedance signal 302 includes thoracic impedance information about the subject over sixteen days, and the impedance signal 302 correlates with the subject's thoracic fluid level or edema status. A first portion 312 of the thoracic impedance signal 302 can represent an abnormal thoracic impedance magnitude, such as when the subject retains excess fluid or exhibits signs of excess pulmonary fluid. In an example, information about a subject's circadian pattern can be identified using the thoracic impedance signal 302.

The processor circuit 110 can use information about a change in the impedance signal 302 to identify the first treatment event 350. In an example, the first treatment event 350 includes a diuresis treatment that begins at 313, and the subject's thoracic impedance signal 302 changes (increases) over the duration of the first treatment event 350. Prior to the diuresis treatment at 313, the subject's average thoracic impedance magnitude can be depressed relative to a reference thoracic impedance magnitude, such as due to an elevated thoracic fluid level. The reference thoracic impedance magnitude can be a subject-specific or other specified baseline or "normal" impedance magnitude, such as can be provided using the physiologic status reference generator circuit 260. The diuresis treatment at 313, such as including administration of furosemide, spironolactone, or another drug to help the subject reduce excess thoracic fluid, can result in an increase of the subject's average thoracic impedance magnitude, such as during the first treatment event 350. In the example of FIG. 3, the subject's average thoracic impedance can continue to increase over the post-treatment interval 309, such as after discharge from the hospital or after a treatment ceases at 316. In an example, the processor circuit 110 can identify a candidate treatment cessation event, such as by identifying a difference between a trend in the impedance signal during the first treatment event 350 and a trend in the impedance signal during the post-treatment interval 309.

The respiratory tidal volume signal 303 can be received using the respiration sensor 206. The respiratory tidal volume signal 303 can represent a smoothed or an average tidal volume signal received from one or more sources and representative of a subject's tidal volume over time. For example, the respiratory tidal volume signal 303 can represent a subject's tidal volume that is sampled or measured intermittently, and the resulting samples can be averaged to provide a daily average tidal volume signal for the subject. In the example of FIG. 3, the tidal volume signal 303 includes respiratory tidal volume information about the subject over about sixteen days. In an example, the subject's respiratory tidal volume represents a subject's lung capacity, such as can indicate a subject's thoracic fluid level or edema status. A first portion 317 of the respiratory tidal volume magnitude can represent an abnormal or reduced tidal volume magnitude, such as when the subject retains excess fluid or exhibits signs of edema.

The subject's respiratory tidal volume signal 303 can indicate a subject physiologic response to a therapy that is provided during the first treatment event 350. In an example, a diuresis treatment begins at the onset 313 of the first treatment event 350. Prior to the diuresis treatment, the subject's average respiratory tidal volume can be depressed relative to a reference tidal volume, such as due to an elevated thoracic fluid level. The reference respiratory tidal volume magnitude can be a subject-specific or other specified baseline or "normal" tidal volume. In response to the diuresis treatment, the subject's average respiratory tidal volume can increase, such as during the first treatment event 350 or over a post-treatment interval 309. In the example of FIG. 3, the processor circuit 110 can be used to identify that the subject's respiratory tidal volume magnitude trends toward a normal tidal volume magnitude over the post-treatment interval 309 when the subject returns to activities of normal daily life. Even though the subject's edema status may be improving during the first treatment event 350, the subject's respiratory tidal volume magnitude may be relatively depressed during the first treatment event 350 because the subject is mostly sedentary during the treatment event, or due to a detection limitation of the tidal volume sensor itself.

In an example, a rapid shallow breathing index (RBSI) can be calculated using information about the subject's respiratory tidal volume and using respiration frequency information. The respiration frequency information can be determined using, among other things, the respiratory tidal volume signal 303, the thoracic impedance signal 302, or using information from one or more other physiologic sensors. The processor circuit 110 can be configured to identify a candidate treatment event by identifying a trend in a subject's RSBI. For example, the processor circuit 110 can identify a candidate treatment event when an inter-day trend shows an increasing RSBI, and then the RSBI abruptly decreases, such as be due to medical intervention.

The S1 heart sound amplitude signal 304 can be received using the accelerometer 203. The S1 heart sound amplitude signal 304 can represent an S1 heart sound that is intermittently sampled and averaged over time. In the example of FIG. 3, the S1 heart sound signal 304 includes S1 amplitude information about the subject over about sixteen days. The subject's S1 heart sound amplitude can be depressed relative to a baseline S1 heart sound amplitude, such as due to low ventricular myocardial contractility. For example, during the pre-treatment interval 306, the subject's S1 heart sound amplitude can have a first average magnitude 322. The subject can exhibit the first average magnitude 322 until after the onset 313 of the first treatment event 350, and until after administration of an inotropic drug at 323. In response to the inotrope administration at 323, the subject's ventricular contractility can improve, resulting in an increase in average S1 heart sound amplitude over an improvement duration 324. The subject's S1 heart sound amplitude can reach a second average heart sound magnitude 325, such as corresponding to a subject's reference or normal S1 heart sound amplitude.

FIG. 4 illustrates generally an example 400 that includes information about multiple physiologic signals sensed from a subject over multiple days. The example 400 includes information about the multiple physiologic signals before, during, and after a second treatment event 450. The processor circuit 110 can be configured to use information about one or more of the multiple physiologic signals to identify a timing of the second treatment event 450. In the example of FIG. 4, the second treatment event 450 includes a 12-hour in-clinic treatment of a subject's acute HF symptoms, such as edema. The example of FIG. 4 includes multiple physiologic signals, including a posture signal 401, an impedance signal 402, a tidal volume signal 403, and an S3 heart sound amplitude signal 404.

The posture signal 401 can be received using the accelerometer 203. The accelerometer 203 can be configured to provide a signal indicative of a subject's physical orientation. For example, the signal can include information about different subject postures such as upright, supine, or lying down left or right side postures. In the example of FIG. 4, a relative minimum in the posture signal 401 can correspond to a supine position, and a relative maximum can correspond to an upright position. A subject's circadian pattern can be optionally determined using information about the subject's posture from the posture signal 401. For example, during a pre-treatment interval 406 including multiple days, several sleep/wake cycles can be inferred based on the subject's periodic supine and upright positions. Referring again to FIG. 3, a cessation or emergence of a subject's circadian pattern can correspond respectively to an onset 313 of a treatment event 350 or a discharge from a hospital at an end 310 of the first treatment event 350. In the example of FIG. 4, a hospital discharge event at 407 can occur soon after an onset 413 of the second treatment event 450, resulting in a less disruption of the subject's circadian pattern. Thus, in the example of FIG. 4, the subject's circadian pattern can appear to be relatively consistent or normal before, during, and after the second treatment event 450.

The impedance signal 402 can include a single thoracic impedance signal from a subject, or the impedance signal 402 can represent an average or composite of multiple thoracic impedance signals measured from a subject body. For example, multiple thoracic impedance signals corresponding to multiple different thoracic impedance vectors in the subject can be averaged to provide a trend indicative of a subject's average thoracic impedance magnitude over multiple days 411. Prior to a diuresis treatment at 412, the subject's average thoracic impedance magnitude can be reduced relative to the subject's baseline impedance magnitude, such as due to the subject's elevated thoracic fluid level. At 412, the subject can receive the diuresis treatment to help the subject to expel excess thoracic fluid. As the subject responds favorably to the diuretic, the subject's average thoracic impedance magnitude can increase as a result of the corresponding decrease in thoracic fluid. After the diuresis treatment at 412, and after the second treatment event 450 concludes, the subject's average thoracic impedance magnitude can remain stable for several days and then decline. In an example, a post-treatment decline can indicate an over-diuresis of the subject.

The respiratory tidal volume signal 403 can include information about a subject's respiratory tidal volume over time. Prior to the diuresis treatment at 412, the subject's initial average respiratory tidal volume magnitude 417 can be reduced relative to a normal tidal volume magnitude, such as due to a subject's elevated thoracic fluid level. At 412, the subject can receive the diuresis treatment to help the subject to expel excess thoracic fluid and relieve congestive symptoms. As the subject responds favorably to the diuretic, the subject's average respiratory tidal volume magnitude can increase as a result of the corresponding decrease in thoracic fluid. After the diuresis treatment at 412, and after the second treatment event 450 concludes, the subject's average tidal volume magnitude can remain stable over the post-treatment interval 414.

The presence of an S3 heart sound can indicate an increase in a subject's LV filling pressure or a decrease in a subject's ejection fraction. In some examples, the magnitude of an S3 heart sound signal amplitude can be reduced by improving the contractility of the heart. In the example of FIG. 4, the S3 heart sound signal 404 can indicate an S3 heart sound signal amplitude over the pre-treatment interval 406. In response to the treatment event 450, the S3 amplitude can decrease over the post-treatment interval 414. In an example, the decreased S3 amplitude can indicate improved ventricular contractility of the subject's heart.

FIG. 5 illustrates generally an example 500 that includes information about multiple physiologic signals sensed from a subject over multiple days. The multiple physiologic signals include an acceleration signal 501, a thoracic impedance signal 502, and a respiratory tidal volume signal 503. The example 500 includes information about the multiple physiologic signals before, during, and after a third treatment event 550 that includes a multiple-day hospitalization. The third treatment event 550 includes, among other things, four diuretic agent administration events 511, 512, 513, and 514, corresponding respectively to four different days.

The acceleration signal 501 indicates generally a subject's physical activity level over sixteen days. The physical activity level information is sampled and the results can optionally be smoothed and plotted as shown in FIG. 5. In the example of FIG. 5, the acceleration signal 501 has a first magnitude 510 that is substantially constant before, during, and immediately after the third treatment event 550. At or around day 11, the magnitude of the acceleration signal 501 begins to show increased variation 520, such as corresponding to an increase in the subject's physical activity level, and an emergence of the subject's circadian pattern. The processor circuit 110 can identify and use information about the increased variation in the subject's physical activity level to indicate a candidate treatment event, such as the third treatment event 550.

The thoracic impedance signal 502 indicates generally a subject's thoracic impedance magnitude, which correlates generally with the subject's thoracic fluid level or edema status. In the example of FIG. 5, the thoracic impedance signal 502 has a first impedance magnitude 530 that is substantially constant before the third treatment event 550. The first impedance magnitude 530 indicates generally a reduced impedance magnitude, such as due to the presence of excess fluid in the subject's thoracic region. In response to administration of the diuretic agents at 511, 512, 513, and 514, the magnitude 535 of the subject's thoracic impedance increases. After the third treatment event 550 terminates, the thoracic impedance signal 502 reached a second impedance magnitude 540 that is substantially constant and is greater than the first impedance magnitude 530. The second impedance magnitude 540 can indicate generally a decrease in the subject's thoracic fluid level.

The respiratory tidal volume signal 503 indicates generally a subject's respiratory tidal volume, which correlates generally with the subject's health status or edema status. In the example of FIG. 5, the respiratory tidal volume signal 503 has a first magnitude 560 that is substantially constant before, during, and immediately after the third treatment event 550. At or around day 11, the magnitude of the respiratory tidal volume signal 503 begins to show increased variation, such as corresponding to an increased tidal volume. In some examples, increased tidal volume can indicate, among other things, an increase in the subject's physical activity level, or a reduction in a subject's thoracic fluid level.

Figure 6:
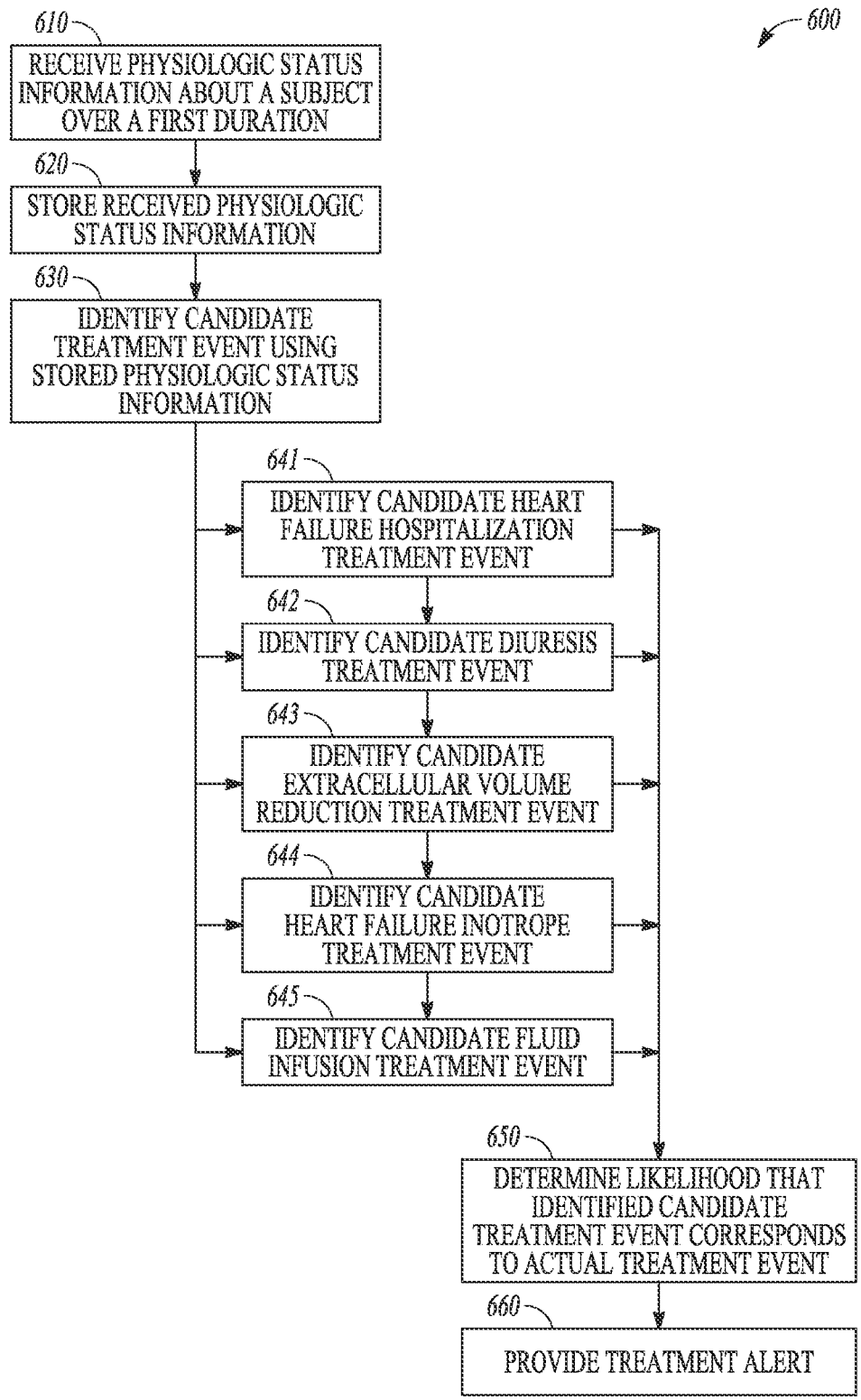
FIG. 6 illustrates generally an example of a method that can include identifying a candidate treatment event using stored physiologic signal information.

FIGS. 6-9 illustrate generally examples that include identifying a candidate treatment event using information about previously-acquired physiologic signal information. Referring now to FIG. 6, an example 600 includes using a processor circuit, such as the processor circuit 110 in the IMD 105 or using another processor circuit in the external system 125, to identify a candidate treatment event using physiologic status information from a subject. The following discussion of the example 600 refers to the example 300 of FIG. 3, however the example 600 can be alternatively or additionally applied to other physiologic signal information than is included in the example 300.

At 610, physiologic status information about a subject can be received over a first interval or duration. The physiologic status information includes information about the subject that can be sensed or measured using one or more of the physiologic sensors 201-209. The first duration can include several hours or days, and the first duration optionally includes a treatment event such as a hospitalization, diuretic administration, or other therapy event. With reference to FIG. 3, the physiologic status information received at 610 can include one or more of the acceleration signal 301, the thoracic impedance signal 302, the respiratory tidal volume signal 303, or the S1 heart sound amplitude signal 304. The first duration can correspond to the sixteen days illustrated in the example of FIG. 3.

At 620, the physiologic status information received at 610 can be stored. For example, the physiologic status information can be stored in the memory circuit 240 of the IMD 105, or in an external memory circuit in the external system 125. In an example, the physiologic status information is stored in the memory circuit 240 as a string of samples, or the information is stored using a histogram, or the information is stored using a data compression or data volume reduction technique.

At 630, a candidate treatment event can be identified using the treatment detection circuit 280 and using the physiologic status information stored at 620. In the example of FIG. 3, a candidate treatment event can be identified at 313 when the subject's circadian pattern (identified using the acceleration signal 301, discussed above) is interrupted. Identifying the candidate treatment event at 630 can include one or more of identifying an onset of a treatment event, identifying a treatment in progress, or identifying a conclusion of a treatment event. For example, referring to FIG. 3, the conclusion at 310 of the first treatment event 350 can correspond to an emergence of the subject's circadian pattern after one or more periods during which relatively low levels of circadian activity were detected.

At 641-645, the candidate treatment event identified at 630 can be categorized. For example, at 641, the candidate treatment event can be identified as a heart failure hospitalization treatment event. At 642, the candidate treatment event can be identified as a diuresis treatment event. At 643, the candidate treatment event can be identified as a extracellular volume reduction treatment event. At 644, the candidate treatment event can be identified as a heart failure inotrope treatment event. At 645, the candidate treatment event can be identified as a fluid infusion treatment event. One or more other types of treatment can alternatively or additionally be identified.

The type or types of physiologic signal used to identify the candidate treatment event at 630 can be used to categorize the candidate treatment event at 641-645. For example, referring to FIG. 3, when information about a subject's circadian pattern is used together with information about the subject's thoracic impedance, the processor circuit 110 can identify the candidate treatment event as a heart failure hospitalization treatment event at 641, such as when the circadian pattern is interrupted for a several day interval and the subject's thoracic impedance magnitude shows an increasing trend over the same several day interval. In an example, when information about a subject's thoracic impedance magnitude is used together with information about the subject's respiratory tidal volume, the processor circuit 110 can identify the candidate treatment event as one or more of a heart failure hospitalization treatment event at 641 and as a diuresis treatment event at 642, such as when the subject's thoracic impedance magnitude shows a steady improvement over multiple days, and the subject's respiratory tidal volume shows a marked improved three to four days after the onset of the improvement in the subject's thoracic impedance magnitude.

At 650, the processor circuit 110 can determine a likelihood that a candidate treatment event corresponds to an actual treatment event. For example, the processor circuit 110 can identify multiple different physiologic status trends. If each of the multiple physiologic status trends indicates a candidate treatment event corresponding to the same previous time interval, then the processor circuit 110 can determine a high likelihood or confidence that the identified event corresponds to an actual treatment event. In contrast, if only a single physiologic status trend indicates a candidate treatment event, then the processor circuit 110 can determine a low likelihood that the identified event corresponds to an actual treatment event.

Some physiologic status information can more reliably indicate an actual treatment event. For example, relatively quick a change in a subject's thoracic impedance magnitude information can, under some circumstances, be a better indicator of a treatment event than a subject's physical activity level. Accordingly, the processor circuit 110 can differently weight the likelihood determined at 650 depending on the type of data used to identify the candidate event.

At 660, a treatment alert can optionally be provided. The treatment alert can be provided to a subject or clinician, for example, using an interface communicatively coupled to the IMD 105, or the treatment alert can be generated and stored, for example, locally in the IMD 105 or in the external system 125. The treatment alert can include, among other things, one or more of the candidate treatment event identified at 630, timing information corresponding to the candidate treatment event, a category of the candidate treatment event identified at 641-645, or a likelihood identified at 650. In an example, the treatment alert includes all or a portion of the physiologic information about the subject corresponding to the candidate treatment event, such as including physiologic signal information about the subject from an interval before, during, or after the identified candidate treatment event.

Figure 7:
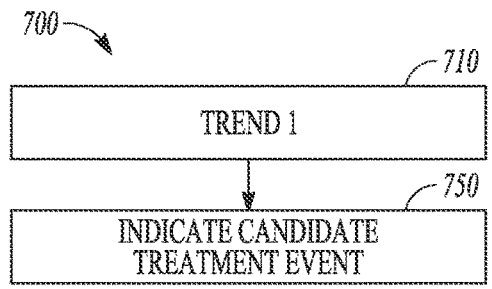
FIG. 7 illustrates generally an example of a method that can include identifying a candidate treatment event using a first physiologic signal trend.

FIG. 7 illustrates generally an example 700 that can include using a processor circuit to identify a first trend in a physiologic signal at 710, and using the same or a different processor circuit to indicate a candidate treatment event at 750. At 710, identifying a first trend in a physiologic signal can include identifying an improvement or decline in a subject health status. The first trend can include one of an emergence of a circadian pattern, an increase in a subject's thoracic impedance magnitude, an increase in a subject's respiratory tidal volume, or a decrease in an occurrence of a subject's S3 heart sound, among other things.

At 750, a candidate treatment event can be indicated at a time, or at a range of times, that correspond to the trend identified at 710. Depending on the type or category of trend identified at 710, the candidate treatment event can be indicated at the onset of the trend, at the conclusion of the trend, or at some other point in time corresponding to the trend.

For example, referring to FIG. 3, identifying the first trend at 710 can include identifying the increase in the subject's respiratory tidal volume during and after the first treatment event 350. At 750, a candidate treatment event can be indicated, for example, at 313 corresponding to an initial increase in the subject's respiratory tidal volume. The candidate treatment event can be indicated at the conclusion of the first treatment event 350 corresponding to the sharp increase in the subject's respiratory tidal volume. In an example, the candidate treatment event can be indicated as a duration that includes an interval before and after the sharp increase in the subject's respiratory tidal volume.

Figure 8:
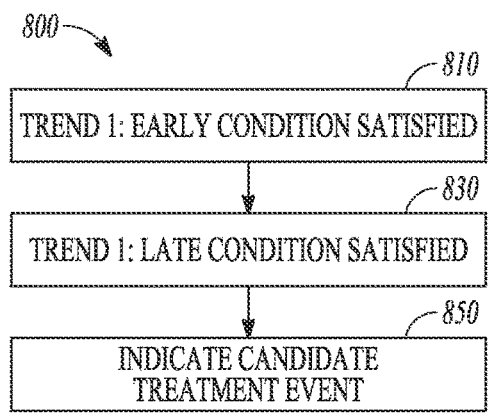
FIG. 8 illustrates generally an example of a method that can include identifying a candidate treatment event using early and late conditions of a first physiologic signal.

FIG. 8 illustrates generally an example 800 that can include using a processor circuit to identify whether an early condition in a first trend is satisfied at 810, using the same or a different processor circuit to identify whether a late condition in the first trend is satisfied at 830, and using the same or a different processor circuit to indicate a candidate treatment event at 850, for example, when the early and late conditions are both satisfied.

At 810, identifying an early condition in the first trend includes identifying a first or initial characteristic of a physiologic signal. At 830, identifying a late condition in the first trend includes identifying a second or subsequent characteristic of the same physiologic signal. In an example, the first trend includes the respiratory tidal volume signal 303. The early condition can include a gradual increase in the subject's respiratory tidal volume over multiple days, such as at the onset 313 of the first treatment event 350. The late condition can include a rapid increase in the subject's respiratory tidal volume over multiple days, such as at the conclusion of the first treatment event 350. At 850, a processor circuit can indicate a candidate treatment event at a time or at a range of times that correspond to the early and late conditions identified at 810 and 830.

Figure 9:
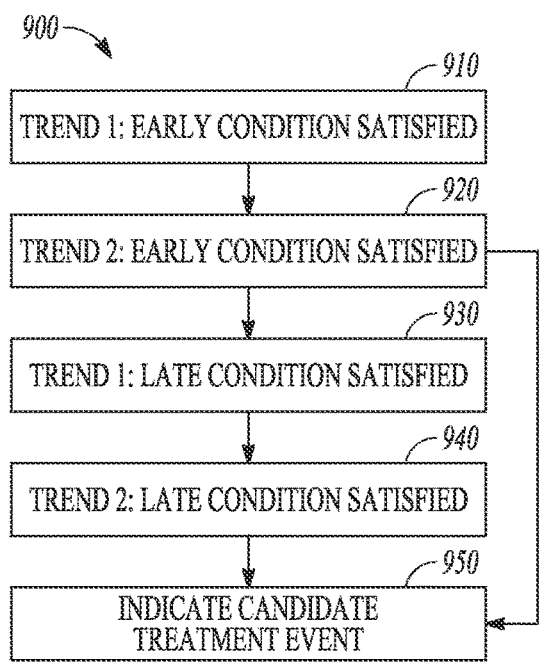
FIG. 9 illustrates generally an example of a method that can include identifying a candidate treatment event using early and late conditions from multiple physiologic signals.

Referring now to FIG. 9, an example 900 includes using one or more processor circuits to identify whether early and late conditions in two or more trends are satisfied. At 910, identifying an early condition in a first trend includes identifying a first or initial characteristic of a first physiologic signal. At 920, identifying an early condition in a second trend includes identifying a first or initial characteristic of a second physiologic signal. In an example, when early conditions from two or more trends are satisfied, a candidate treatment event can be identified at 950. The first and second physiologic signals can be different types of signals, such as received from different sensors measuring different aspects of a subject's physiologic status. The early conditions can be specific to the type of signal. For example, an early condition for a physical activity level signal can include a relative cessation of a subject's circadian pattern, or an early condition for a thoracic impedance signal can include a decrease in a subject's thoracic impedance magnitude.

At 930, identifying a late condition in the first trend includes identifying a second or subsequent characteristic of the first physiologic signal. At 940, identifying a late condition in the second trend includes identifying a second or subsequent characteristic of the second physiologic signal. In an example, when the early condition and the late condition from each of the two or more trends are satisfied, a candidate treatment event can be identified at 950.

In an example, the first trend includes a subject's circadian pattern determined using information about a subject physical activity level, and the second trend includes the subject's thoracic impedance magnitude. At 910, an early condition is satisfied for the first trend when the first trend shows a relative cessation of the subject's circadian pattern. At 920, an early condition is satisfied for the second trend when the second trend shows rapid thoracic fluid loss, as evidenced by a sharp increase in the subject's thoracic impedance magnitude. At 930, a late condition is satisfied for the first trend when the subject's circadian pattern improves or emerges, such as several days after the early condition was satisfied at 910. At 940, a late condition is satisfied for the second trend when the subject's thoracic impedance magnitude reaches a new steady-state value, such as can be determined using the physiologic status reference generator circuit 260. At 950, a candidate treatment event can be indicated at a time or at a range of times that correspond to the early and late conditions identified at 910, 920, 930, and 940.

VARIOUS NOTES & EXAMPLES

Example 1 can include or use subject matter (such as an apparatus, a method, a means for performing acts, or a device readable medium including instructions that, when performed by the device, can cause the device to perform acts), such as can include or use a system for detecting a previous or ongoing treatment of a subject, the system including a first physiologic sensor configured to sense a physiologic signal from the subject, and a treatment detection circuit. In Example 1, the treatment detection circuit can include a memory circuit configured to store information about the physiologic signal from the first physiologic sensor, and a processor circuit configured to identify a candidate treatment event for the subject using the information about the physiologic signal stored in the memory circuit.

Example 2 can include, or can optionally be combined with the subject matter of Example 1, to optionally include the treatment detection circuit, including a heart failure (HF) hospitalization treatment detection circuit. In Example 2, the processor circuit can be configured to identify a candidate HF hospitalization treatment event for the subject using the information about the physiologic signal stored in the memory circuit.

Example 3 can include, or can optionally be combined with the subject matter of one or any combination of Examples 1 or 2 to optionally include the treatment detection circuit, including a diuresis treatment detection circuit. In Example 3, the processor circuit can be configured to identify a candidate diuresis treatment event for the subject using the information about the physiologic signal stored in the memory circuit.

Example 4 can include, or can optionally be combined with the subject matter of one or any combination of Examples 1 through 3 to optionally include the treatment detection circuit, including an extracellular volume reduction treatment detection circuit. In Example 4, the processor circuit can be configured to identify a candidate extracellular volume reduction treatment event for the subject using the information about the physiologic signal stored in the memory circuit.

Example 5 can include, or can optionally be combined with the subject matter of one or any combination of Examples 1 through 4 to optionally include the treatment detection circuit, including a heart failure (HF) inotrope treatment detection circuit. In Example 5, the processor circuit can be configured to identify a candidate inotropic treatment event for the subject using the information about the physiologic signal stored in the memory circuit.

Example 6 can include, or can optionally be combined with the subject matter of Example 5, to optionally include the first physiologic sensor, including a transducer configured to sense a heart sound signal from the subject. In Example 6, the memory circuit can be configured to store information about the heart sound signal from the transducer, and the processor circuit can be configured to identify the candidate inotropic treatment event for the subject using the information about the heart sound signal.

Example 7 can include, or can optionally be combined with the subject matter of one or any combination of Examples 1 through 6 to optionally include the treatment detection circuit, including a fluid infusion detection circuit. In Example 7, the processor circuit can be configured to identify a candidate fluid infusion event for the subject using the information about the physiologic signal stored in the memory circuit.

Example 8 can include, or can optionally be combined with the subject matter of Example 7, to optionally include the first physiologic sensor, including an impedance sensor configured to sense a thoracic impedance signal from the subject. In Example 8, the memory circuit can be configured to store information about the thoracic impedance signal from the impedance sensor, and the processor circuit can be configured to identify the candidate fluid infusion event for the subject using the information about the thoracic impedance signal.

Example 9 can include, or can optionally be combined with the subject matter of one or any combination of Examples 1 through 8 to optionally include the first physiologic sensor configured to sense a physiologic signal that includes information about the subject's circadian rhythm. In Example 9, the processor circuit can be configured to identify the candidate treatment event by identifying a change in the subject's circadian rhythm.

Example 10 can include, or can optionally be combined with the subject matter of Example 9, to optionally include the first physiologic sensor, including an accelerometer that is configured to sense the physiologic signal including being configured to sense the information about the subject's circadian rhythm using information about the subject's posture and using information about the subject's physical activity level.

Example 11 can include, or can optionally be combined with the subject matter of one or any combination of Examples 1 through 10 to optionally include the first physiologic sensor configured to sense a physiologic signal that includes information about the subject's thoracic impedance. In Example 11, the processor circuit is configured to identify the candidate treatment event using an inter-day trend in the information about the subject's thoracic impedance.

Example 12 can include, or can optionally be combined with the subject matter of one or any combination of Examples 1 through 11 to optionally include the first physiologic sensor configured to sense a physiologic signal that includes information about the subject's respiration status. In Example 12, the processor circuit can be configured to identify the candidate treatment event using information about a change in the information about the subject's respiration status.

Example 13 can include, or can optionally be combined with the subject matter of Example 12, to optionally include the processor circuit configured to identify the candidate treatment event by identifying an inter-day trend in the subject's tidal volume, the tidal volume determined using the information about the subject's respiration status.

Example 14 can include, or can optionally be combined with the subject matter of Example 12, to optionally include the processor circuit configured to identify the candidate treatment event by identifying an inter-day trend in the subject's rapid shallow breathing index (RSBI), the RSBI determined using respiration frequency information and tidal volume information from the subject's respiration status.

Example 15 can include, or can optionally be combined with the subject matter of one or any combination of Examples 1 through 14 to optionally include the first physiologic sensor configured to sense a physiologic signal that includes information about a heart sound of the subject. In Example 15, the processor circuit is configured to identify the candidate treatment event by identifying a change in the information about the subject's heart sound.

Example 16 can include, or can optionally be combined with the subject matter of Example 15, to optionally include the first physiologic sensor configured to sense information about an S1 heart sound amplitude of the subject. In Example 16, the processor circuit can be configured to identify the candidate treatment event by identifying a change in the information about the subject's S1 heart sound amplitude.

Example 17 can include, or can optionally be combined with the subject matter of Example 15, to optionally include the first physiologic sensor configured to sense information about an S3 heart sound timing or an S3 heart sound amplitude of the subject. In Example 17, the processor circuit can be configured to identify the candidate treatment event by identifying a change in the information about the subject's S3 heart sound timing or S3 heart sound amplitude.

Example 18 can include, or can optionally be combined with the subject matter of one or any combination of Examples 1 through 17 to optionally include an impedance sensor configured to sense a thoracic impedance signal from the subject, and a respiration sensor configured to sense a respiration status signal from the subject. In Example 18, the first physiologic sensor can include an accelerometer configured to sense information about the subject's circadian rhythm, and the processor circuit can be configured to identify a circadian pattern signal from the subject. In Example 18, the memory circuit can be configured to store information about each of the thoracic impedance signal, the respiration status signal, and the circadian pattern signal from the subject. In Example 18, the processor circuit can be configured to identify the candidate treatment event using the information stored in the memory circuit about the thoracic impedance signal, the respiration status signal, or the circadian pattern signal from the subject.

Example 19 can include, or can optionally be combined with the subject matter of Example 18, to optionally include the processor circuit configured to identify the candidate treatment using the information stored in the memory circuit about the thoracic impedance signal, the respiration status signal, and the circadian pattern signal from the subject.

Example 20 can include, or can optionally be combined with the subject matter of one or any combination of Examples 1 through 19 to optionally include an alert generator circuit, wherein the alert generator circuit is configured to locally store or externally communicate information about the candidate treatment event identified by the processor circuit.

Example 21 can include, or can optionally be combined with the subject matter of one or any combination of Examples 1 through 20 to optionally include a physiologic status reference generator circuit configured to update a physiologic status reference indication about the subject using information received intermittently from the first physiologic sensor. In Example 21, the reference generator circuit can be configured to omit or differently weight information from the first physiologic sensor that corresponds to a candidate treatment event identified by the processor circuit.

Example 22 can include, or can optionally be combined with the subject matter of one or any combination of Examples 1 through 21 to optionally include the processor circuit configured to determine a likelihood that the identified candidate treatment event corresponds to an actual previous HF hospitalization treatment event or diuresis treatment event.

Example 23 can include, or can optionally be combined with the subject matter of one or any combination of Examples 1 through 22 to optionally include an implantable medical device that includes the detection circuit. In Example 23, the first physiologic sensor can be communicatively coupled to the implantable medical device.

Example 24 can include, or can optionally be combined with the subject matter of one or any combination of Examples 1 through 23 to optionally include the processor circuit configured to identify the candidate treatment event in response to a user input request.

Example 25 can include or use subject matter (such as an apparatus, a method, a means for performing acts, or a device readable medium including instructions that, when performed by the device, can cause the device to perform acts), such as can include or use a method for detecting a previous or ongoing treatment of a subject. The method of Example 25 can include receiving, using an ambulatory medical device, physiologic status information about the subject over a first duration from a first physiologic sensor, recording the received physiologic status information about the subject using a memory circuit coupled to the ambulatory medical device, and identifying a candidate treatment event for the subject using a processor circuit and the recorded physiologic status information about the subject from the memory circuit.

Example 26 can include, or can optionally be combined with the subject matter of Example 24, to optionally include identifying the candidate treatment event, including identifying a candidate HF hospitalization treatment using the processor circuit and using the recorded physiologic status information about the subject from the memory circuit.

Example 27 can include, or can optionally be combined with the subject matter of Example 26, to optionally include identifying the candidate HF hospitalization treatment, including identifying at least one of a subject thoracic surgery, a subject pocket adjustment of the ambulatory medical device, or a programming change to the ambulatory medical device.

Example 28 can include, or can optionally be combined with the subject matter of one or any combination of Examples 25 through 27 to optionally include identifying the candidate treatment, including identifying a candidate diuresis treatment using the processor circuit and using the recorded physiologic status information about the subject from the memory circuit.

Example 29 can include, or can optionally be combined with the subject matter of one or any combination of Examples 25 through 28 to optionally include one of detecting a hospitalization event or receiving a user input. In Example 29, identifying the candidate treatment event can be in response to the detected hospitalization event or the received user input.

Example 30 can include, or can optionally be combined with the subject matter of one or any combination of Examples 25 through 29 to optionally include identifying the candidate treatment, including identifying, in the recorded physiologic status information, a deviation from a reference physiologic status of the subject.

Example 31 can include, or can optionally be combined with the subject matter of one or any combination of Examples 25 through 30 to optionally include determining a likelihood that the identified candidate treatment event corresponds to an actual treatment event, and, when the likelihood exceeds a specified threshold likelihood, providing information about the identified candidate treatment event to a patient interface or to a clinician interface.

Example 32 can include, or can optionally be combined with the subject matter of one or any combination of Examples 25 through 31 to optionally include recording the received physiologic status information about the subject, including recording information about the subject's circadian pattern over the first duration using the first physiologic sensor. In Example 32, identifying the candidate treatment event can include identifying a change in the subject's circadian pattern using the recorded information about the subject's circadian pattern.

Example 33 can include, or can optionally be combined with the subject matter of one or any combination of Examples 25 through 32 to optionally include recording the received physiologic status information about the subject, including recording information about the subject's circadian pattern over the first duration using the first physiologic sensor. In Example 33, identifying the candidate treatment event using the processor circuit can include using the processor circuit to identify a relationship between a reference and at least one of a timing characteristic of the subject's circadian pattern, a severity characteristic of the subject's circadian pattern, or a likelihood that a change in the subject's circadian rhythm indicates an actual HF treatment event.

Example 34 can include, or can optionally be combined with the subject matter of one or any combination of Examples 25 through 33 to optionally include recording the received physiologic status information about the subject, including recording information about the subject's thoracic impedance over the first duration using the first physiologic sensor. In Example 34, identifying the candidate treatment event using the processor circuit can include using the processor circuit to identify at least one of a relationship between a reference and a magnitude of the subject's thoracic impedance, a change rate characteristic of the subject's thoracic impedance magnitude, or a likelihood that a change in the subject's thoracic impedance magnitude indicates an actual HF treatment event.

Example 35 can include, or can optionally be combined with the subject matter of one or any combination of Examples 25 through 34 to optionally include recording the received physiologic status information about the subject, including recording information about the subject's respiration status over the first duration using the first physiologic sensor. In Example 35, identifying the candidate treatment event using the processor circuit can include using the processor circuit to identify a relationship between a reference and at least one of a timing characteristic of the subject's tidal volume, the subject's average tidal volume, the subject's rapid shallow breathing index, a change rate characteristic of the subject's tidal volume, or a likelihood that a change in the subject's tidal volume indicates an actual HF treatment event.

Example 36 can include, or can optionally be combined with the subject matter of one or any combination of Examples 25 through 35 to optionally include recording the received physiologic status information about the subject, including recording information about at least one of the subject's heart sounds over the first duration using the first physiologic sensor. In Example 36, identifying the candidate treatment event using the processor circuit can include using the processor circuit to identify a relationship between a reference and at least one of a timing characteristic of the subject's at least one heart sound, the subject's average heart sound amplitude of the at least one heart sound, a change rate characteristic of the subject's at least one heart sound amplitude or timing, or a likelihood that a change in the subject's at least one heart sound characteristic indicates an actual HF treatment event.

Example 37 can include, or can optionally be combined with the subject matter of one or any combination of Examples 25 through 36 to optionally include identifying the candidate treatment event using the processor circuit, including identifying an initial physiologic status characteristic using the subject's physiologic status information from a first portion of the first duration, identifying a subsequent physiologic status characteristic using the subject's physiologic status information from a subsequent second portion of the first duration, and identifying the candidate treatment event using information about a change from the initial physiologic status characteristic to the subsequent physiologic status characteristic.

Example 38 can include or use subject matter (such as an apparatus, a method, a means for performing acts, or a device readable medium including instructions that, when performed by the device, can cause the device to perform acts), such as can include or use a system including an ambulatory medical device, and the ambulatory medical device can include a data input configured to receive a physiologic signal from a physiologic sensor, the physiologic sensor configured to sense information about a subject's physiologic status, and a memory circuit configured to store information about the physiologic signal received using the data input. Example 38 can include a processor circuit configured to identify a candidate treatment event using the information about the physiologic signal stored in the memory circuit.

Example 39 can include, or can optionally be combined with the subject matter of Example 38, to optionally include the processor circuit as a portion of the ambulatory medical device.

Example 40 can include, or can optionally be combined with the subject matter of one or any combination of Examples 38 or 39 to optionally include the processor circuit configured to identify a candidate HF hospitalization treatment for the subject using the information about the physiologic signal stored in the memory circuit.

Example 41 can include, or can optionally be combined with the subject matter of one or any combination of Examples 38 through 40 to optionally include the processor circuit configured to identify a candidate previous HF diuresis treatment for the subject using the information about the physiologic signal stored in the memory circuit.

Example 42 can include, or can optionally be combined with the subject matter of one or any combination of Examples 38 through 41 to optionally include the processor circuit configured to identify a candidate previous fluid infusion for the subject using the information about the physiologic signal stored in the memory circuit.

Example 43 can include, or can optionally be combined with the subject matter of one or any combination of Examples 38 through 41 to optionally include the processor circuit configured to identify a candidate HF hospitalization treatment or a candidate diuresis treatment by identifying, in the stored information about the physiologic signal, a deviation from a reference physiologic status of the subject.

Example 44 can include, or can optionally be combined with the subject matter of one or any combination of Examples 38 through 42 to optionally include the data input configured to receive multiple physiologic signals from respective multiple physiologic sensors configured to sense information about the subject physiologic status.

Example 45 can include, or can optionally be combined with the subject matter of Example 44, to optionally include the multiple physiologic sensors, the sensors including two or more of an accelerometer configured receive a posture or physical activity signal indicative of the subject's circadian pattern, a thoracic impedance sensor configured to receive a thoracic impedance signal indicative of the subject's thoracic impedance, or a respiration sensor configured to receive a respiration signal indicative of the subject's respiration status. In Example 45, the memory circuit can be configured to store information about the posture or physical activity signal, the thoracic impedance signal, or the respiration signal, and the processor circuit can be configured to identify a candidate previous HF treatment event using the information about two or more of the posture or physical activity signal, the thoracic impedance signal, or the respiration signal stored in the memory circuit.

Example 46 can include, or can optionally be combined with the subject matter of one or any combination of Examples 38 through 45 to optionally include, in the ambulatory medical device, a therapy control circuit and a therapy output circuit configured to generate a subject therapy using a therapy parameter received from the therapy control circuit. In Example 46, the therapy control circuit can be configured to update the therapy parameter using information about the identified candidate treatment event.

Example 47 can include, or can optionally be combined with the subject matter of one or any combination of Examples 38 through 46 to optionally include the processor circuit configured to identify the candidate treatment event in response to a user input to the ambulatory medical device.

Example 48 can include, or can optionally be combined with the subject matter of one or any combination of Examples 38 through 47 to optionally include the processor circuit configured to generate a treatment alert that includes physiologic signal information other than the information about the physiologic signal used by the processor circuit to identify the candidate treatment event.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system for detecting a previous or ongoing treatment of a subject, the system comprising:
 a first physiologic sensor configured to sense a physiologic signal from the subject; and
 a previous treatment detection circuit, the treatment detection circuit including:
  a memory circuit configured to store information about the physiologic signal from the first physiologic sensor; and
  a processor circuit configured to identify a candidate previous treatment event for the subject using the information about the physiologic signal stored in the memory circuit.

2. The system of claim 1, wherein the previous treatment detection circuit includes a heart failure (HF) hospitalization treatment detection circuit, and wherein the processor circuit is configured to identify a candidate previous HF hospitalization treatment event for the subject using the information about the physiologic signal stored in the memory circuit.

3. The system of claim 1, wherein the previous treatment detection circuit includes a diuresis treatment detection circuit, and wherein the processor circuit is configured to identify a candidate previous diuresis treatment event for the subject using the information about the physiologic signal stored in the memory circuit.

4. The system of claim 1, wherein the previous treatment detection circuit includes one of an extracellular volume reduction treatment detection circuit, a heart failure (HF) inotrope treatment detection circuit, and a fluid infusion detection circuit.

5. The system of claim 1, wherein the first physiologic sensor is configured to sense a physiologic signal that includes information about the subject's circadian rhythm, and wherein the processor circuit is configured to identify the candidate previous treatment event by identifying a change in the subject's circadian rhythm.

6. The system of claim 5, wherein the first physiologic sensor includes an accelerometer that is configured to sense the physiologic signal including being configured to sense the information about the subject's circadian rhythm using information about the subject's posture and using information about the subject's physical activity level.

7. The system of claim 1, wherein the first physiologic sensor is configured to sense a physiologic signal that includes information about the subject's thoracic impedance, and wherein the processor circuit is configured to identify the candidate previous treatment event using an inter-day trend in the information about the subject's thoracic impedance.

8. The system of claim 1, wherein the first physiologic sensor is configured to sense a physiologic signal that includes information about the subject's respiration status, and wherein the processor circuit is configured to identify the candidate previous treatment event using information about a change in the information about the subject's respiration status.

9. The system of claim 1, wherein the first physiologic sensor is configured to sense a physiologic signal that includes information about a heart sound of the subject, and wherein the processor circuit is configured to identify the candidate previous treatment event by identifying a change in the information about the subject's heart sound.

10. The system of claim 1, comprising:
 an impedance sensor configured to sense a thoracic impedance signal from the subject; and
 a respiration sensor configured to sense a respiration status signal from the subject;
 wherein the first physiologic sensor includes an accelerometer configured to sense information about the subject's circadian rhythm, wherein the processor circuit is configured to identify a circadian pattern signal from the subject;
 wherein the memory circuit is configured to store information about each of the thoracic impedance signal, the respiration status signal, and the circadian pattern signal from the subject; and
 wherein the processor circuit is configured to identify the candidate previous treatment event using information about a change in at least one of the subject's thoracic impedance, the subject's respiration status, and the subject's circadian pattern, based on the information stored in the memory circuit about the thoracic impedance signal, the respiration status signal, and the circadian pattern signal.

11. The system of claim 1, wherein the processor circuit is configured to determine a likelihood that the identified candidate previous treatment event corresponds to an actual previous HF hospitalization treatment event or diuresis treatment event.

12. A method for detecting a previous or ongoing treatment of a subject, the method comprising:
 receiving, using an ambulatory medical device, physiologic status information about the subject over a first duration from a first physiologic sensor;
 recording the received physiologic status information about the subject using a memory circuit coupled to the ambulatory medical device; and
 identifying a candidate previous treatment event for the subject using a processor circuit and the recorded physiologic status information about the subject from the memory circuit.

13. The method of claim 12, wherein the identifying the candidate previous treatment event includes identifying a candidate HF hospitalization treatment using the processor circuit and using the recorded physiologic status information about the subject from the memory circuit.

14. The method of claim 12, wherein the identifying the candidate previous treatment event includes identifying a candidate diuresis treatment using the processor circuit and using the recorded physiologic status information about the subject from the memory circuit.

15. The method of claim 12, wherein the identifying the candidate previous treatment event includes identifying, in the recorded physiologic status information, first and second changes in the received physiologic status information, the first and second changes occurring within a specified duration.

16. The method of claim 12, comprising determining a likelihood that the identified candidate previous treatment event corresponds to an actual treatment event, and, when the likelihood exceeds a specified threshold likelihood, providing information about the identified candidate treatment event to a patient interface or to a clinician interface.

17. The method of claim 12, wherein the recording the received physiologic status information about the subject includes recording information about the subject's circadian pattern over the first duration using the first physiologic sensor; and
   wherein the identifying the candidate previous treatment event using the processor circuit includes using the processor circuit to identify a relationship between a reference and:
   a timing characteristic of the subject's circadian pattern;
   a severity characteristic of the subject's circadian pattern;
   or a likelihood that a change in the subject's circadian rhythm indicates an actual HF treatment event.

18. The method of claim 12, wherein the recording the received physiologic status information about the subject includes recording information about the subject's thoracic impedance over the first duration using the first physiologic sensor; and
   wherein the identifying the candidate previous treatment event using the processor circuit includes using the processor circuit to identify a relationship between a reference and:
   a magnitude of the subject's thoracic impedance;
   a change rate characteristic of the subject's thoracic impedance magnitude;
   or a likelihood that a change in the subject's thoracic impedance magnitude indicates an actual HF treatment event.

19. The method of claim 12, wherein the recording the received physiologic status information about the subject includes recording information about the subject's respiration status over the first duration using the first physiologic sensor; and
   wherein the identifying the candidate previous treatment event using the processor circuit includes using the processor circuit to identify a relationship between a reference and:
   a timing characteristic of the subject's tidal volume;
   the subject's average tidal volume;
   the subject's rapid shallow breathing index;
   a change rate characteristic of the subject's tidal volume;
   or a likelihood that a change in the subject's tidal volume indicates an actual HF treatment event.

20. A system comprising:
   an ambulatory medical device, comprising:
      a data input configured to receive a physiologic signal from a physiologic sensor, the physiologic sensor configured to sense information about a subject's physiologic status;
      a memory circuit configured to store information about the physiologic signal received using the data input; and
      a processor circuit configured to identify a candidate previous heart failure treatment event using the information about the physiologic signal stored in the memory circuit;
   wherein the processor circuit is configured to identify a likelihood that the identified candidate previous heart failure treatment event indicates an actual previous heart failure treatment event; and
   wherein the processor circuit is configured to generate a treatment alert that includes physiologic signal information other than the information about the physiologic signal used by the processor circuit to identify the candidate previous treatment event.

* * * * *